United States Patent
Samulski et al.

(12)

(10) Patent No.: US 6,670,176 B1
(45) Date of Patent: *Dec. 30, 2003

(54) ADENO-ASSOCIATED VIRUS CAPABLE OF EXPRESSING FACTOR IX PROTEIN AND CELLS COMPRISING THE SAME

(75) Inventors: Richard Jude Samulski, Chapel Hill, NC (US); Christopher E. Walsh, Bethesda, MD (US); Arthur W. Nienhuis, Memphis, TN (US); Johnson M. Liu, Rockville, MD (US); Jeffrey L. Miller, Laurel, MD (US)

(73) Assignees: National Institutes of Health, Rockville, MD (US); University of Pittsburgh, Pittsburgh, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/723,303

(22) Filed: Sep. 30, 1996

Related U.S. Application Data

(60) Division of application No. 08/475,470, filed on Jun. 7, 1995, now Pat. No. 6,268,213, which is a continuation-in-part of application No. 08/344,816, filed on Nov. 23, 1994, now abandoned, which is a continuation of application No. 07/923,418, filed on Jul. 31, 1992, now abandoned, which is a continuation-in-part of application No. 07/893,513, filed on Jun. 3, 1992, now abandoned.

(51) Int. Cl.$^7$ .......................... C12N 15/74; C12N 7/01; A01N 63/00; A61K 48/00
(52) U.S. Cl. .................... 435/320.1; 435/325; 435/455; 435/457; 435/235.1; 435/236; 435/456; 514/44; 424/93.2; 424/93.21
(58) Field of Search ........................ 514/44; 435/455, 435/456, 457, 235.1, 236, 320.1, 325; 424/93.2, 93.21

(56) References Cited

U.S. PATENT DOCUMENTS

| | | | | |
|---|---|---|---|---|
| 5,139,941 | A | 8/1992 | Muzyczka et al. | 435/172.3 |
| 5,173,414 | A | 12/1992 | Lebkowski et al. | 435/172.3 |
| 5,252,479 | A | 10/1993 | Srivastava | 435/235.1 |
| 5,436,146 | A | * 7/1995 | Shenk et al. | 435/235.1 |
| 6,268,213 | B1 | * 7/2001 | Samulski et al. | |

OTHER PUBLICATIONS

Halene et al. Human Gene Therapy Jun. 2000; 11:1259–1267.*
Stocking et al. Bail Clin haematol Sep. 1997; 10:445–465.*
Blood Cells: Encyclopedia Britannica Online. Accessd Dec. 13, 2000.*
Orkin SH, et al. "Report and Recommendations of the Panel to Assess the NIH Investment in Research on Gene Therapy.", Dec. 7, 1995.*
Ohi et al, Gene 89:279–282, 1990.*
Nettelbeck et al. Gene therapy pp. 174–181 vol. 16 no 4 2000.*
Miller et al. progress in transcriptionally targeted and regulatable vectors for genetic therapy pp. 803–815 1997.*
Zink et al. Mammalian genome organization and its implications for the development of gene therapy vectors pp. 1–23 vol. 6 2001.*
Deonarain Ligand–targeted receptor–mediated vectors for gene delivery pp. 53–69 1998.*
Verma et al. Gene therapy promises,problems and prospects pp. 239–242 1997.*
Crystal Transfee of genes to humans:early lessons and obstacles to success 1995 vol. 270 p. 404–410.*
Hermonat et al., "Use of adeno–associated virus as a mammalian DNA cloning vector: Transduction of neomycin resistance into mammalian tissue culture cells", *Proc. Natl. Acad. Sci. USA*, vol. 81, pp. 6466–6470 (Oct. 1984).
Tratschin et al., "A Human Parvovirus, Adeno–Associated Virus, as a Eucaryotic Vector: Transient Expression and Encapsidation of the Procaryotic Gene for Chloramphenicol Acetyltransferase", *Molecular and Cellular Bio.*, pp. 2072–2081 (Oct. 1984).
Orkin, "Molecular Genetics and Potential Gene Therapy", *Clinical Immunology and Immunopathology*, vol. 40, pp. 151–156 (1986).
Nienhuis et al., "Transfer of Genes in Hematopoietic Cells with Retroviral Vectors", *Cell Physiology of Blood*, Chapter 8, pp. 79–89 (1988).
Wondisford et al., "Cloning of the Human Thyrotropin β–Subunit Gene and Transient Expression of Biologically Active Human Thyrotropin after Gene Transfection", *Molecular Endocrinology*, vol. 2, No. 1, pp. 32–39 (1988).
LaFace et al., "Gene Transfer into Hematopoietic Progenitor Cells Mediated by an Adeno–Associated Virus Vector", *Virology*, vol. 162, pp. 483–486 (1988).
Williams, "Gene Transfer and the Prospects for Somatic Gene Therapy", *Hematology/Oncology Clinics of North America*, vol. 2, No. 2, pp. 277–287 (Jun. 1988).

(List continued on next page.)

*Primary Examiner*—Anne M. Wehbe'
*Assistant Examiner*—Q Janice Li
(74) *Attorney, Agent, or Firm*—Pennie & Edmonds LLP; Linda R. Judge, Cell Genesys, Inc.

(57) ABSTRACT

The subject invention concerns a recombinant adeno-associated virus vector characterized as being capable of delivering and expressing at least one mammalian gene into a genome of a mammalian host cell such that the expression of the gene is regulated in a tissue specific manner by cis-acting regulatory and promoter elements of the gene. A method of using this recombinant adeno-associated virus vector for therapeutic purposes is also provided.

8 Claims, 30 Drawing Sheets

OTHER PUBLICATIONS

Gale, "Prospects for Correction of Thalassemia by Genetic Engineering", *Advances and Controversies in Thalassemia Therapy: Bone Marrow Transplantation and Other Approaches*, pp. 141–159 (1989).

Srivastava et al., "Construction of a recombinant human parvovirus B19: Adeno–associated virus 2 (AAV) DNA inverted terminal repeats are functional in an AAV–B19 hybrid virus", *Proc. Natl. Acad. Sci. USA*, vol. 86, pp. 8078–8082 (Oct. 1989).

Sorrentino et al., "A 46 base pair enhancer sequence within the locus activating region is required for induced expression of the gamma–globin gene during erythroid differentiation", *Nucleic Acids Research*, vol. 18, No. 9, pp. 2721–2731 (1990).

Beutler et al., "Gene Transfer in the Treatment of Hematologic Disease", *Exp. Hematol.*, vol. 18, pp. 857–860 (1990).

Ohi et al., "Construction and replication of an adeno–associated virus expression vector that contains human β–globin cDNA", *Gene*, vol. 89, pp. 279–282 (1990).

Novak et al., "High–level β–globin expression after retroviral transfer of locus activation region–containing β–globin gene derivatives into murine erythroleukemia cells", *Proc. Natl. Acad. Sci. USA*, vol. 87, pp. 3386–3390 (May 1990).

Desnick et al., "Human Gene Therapy: Strategies and Prospects for Inborn Errors of Metabolism", *Treatment of Genetic Diseases*, pp. 239–259 (1991).

Nienhuis et al., "Gene Transfer Into Hematopoietic Stem Cells", *Cancer*, vol. 67, pp. 2700–2704 (1991).

Samulski et al., "Targeted integration of adeno–associated virus (AAV) into human chromosome 19", *The EMBO Journal*, vol. 10, No. 12, pp. 3941–3950 (1991).

Ledley, "Clinical Considerations in the Design of Protocols for Somatic Gene Therapy", *Human Gene Therapy*, vol. 2, pp. 77–83 (1991).

Sitaric et al., "Production of a Helper–Free Recombinant Adeno–Associated Virus That Harbors Human Beta–Globin cDNA", FASEB 6(5):6843 (Abstract) (1991).

Walsh et al., "Gene Transfer and High Level Expression of a Human Gamma Globin Gene Mediated by a Novel Adeno–Associated Virus (AAV) Vector", Clinical Research 39(2):325A (Abstract) (1991).

Muzyczka, "Use of Adeno–Associated Virus as a General Transduction Vector for Mammalian Cells", *Current Topics in Microbiology and Immunology*, vol. 158, pp. 97–129 (1992).

Chang et al., "A 36–base–pair core sequence of locus control region enhances retrovirally transferred human β–globin gene expression", *Proc. Natl. Acad. Sci. USA*, vol. 89, pp. 3107–3110 (Apr. 1992).

Miller, "Human gene therapy comes of age", *Nature*, vol. 357, pp. 455–460 (Jun. 1992).

Acland et al., 2001, "Gene therapy restores vision in a canine model of childhood blindness", Nature Genetics 28:92–95.

Bender et al., 1989, "A Majority of Mice Show Long–Term Expression of a Human β–Globin Gene after Retrovirus Transfer into Hematopoietic Stem Cells", Molec. And Cell. Biology 9(4):1426–1434.

Herzog et al., 1999, "Long term correction of canine hemophilia B by gene transfer of blood coagulation factor IX mediated by adeno–associated viral vector", Nature Medicine 5(1):56–63.

Leboulch et al., 1994, "Mutagenesis of Retroviral vectors transducing human β–globin locus control region derivatives results in stable transmission of an active transcriptional structure", EMBO J. 13(13):3065–3076.

Malik et al., 1997, "Recombinant adeno–associated virus mediated a high level of gene transfer but less efficient integration in the K562 human hematopoietic cell line", J. Virol. 71(3):1776–1783.

Ponnazhagan et al., 1997, "Adeno–associated virus type 2–mediated transduction of murine hematopietic cells with long–term repopulating ability and sustained expression of a human globin gene in vivo", J. Virol. 71(4):3098–3104.

Key et al. Evidence for gene transfer and expression of factor IX in haemophilia B patients treated with an AAV vector. Nature Genetics Mar. 2000; 24:257–261.

Snyder et al. Correction of hemophilia B in canine and murine models using recombinant adeno–associated viral vectors. Nat Med. Jan. 1999;5(1):64–70.

Wang et al. Sustained expression of therapeutic level of factor IX in hemophilia B dogs by AAV–mediated gene therapy in liver. Mol Ther. Feb. 2000;1(2):154–8.

\* cited by examiner

ADENO-ASSOCIATED VIRUS CAPABLE OF EXPRESSING FACTOR IX PROTEIN AND CELLS COMPRISING THE SAME

CROSS REFERENCE TO RELATED APPLICATIONS

This is a division of application Ser. No. 08/475,470, filed Jun. 7, 1995 now U.S. Pat. No. 6,268,213.

This is a continuation-in-part application of U.S. application Ser. No. 08/344,816, filed Nov. 23, 1994, now abandoned which is a continuation of U.S. application Ser. No. 07/923,418, filed Jul. 31, 1992, now abandoned, which is a continuation-in-part of U.S. application Ser. No. 07/893,513, filed Jun. 3, 1992, now abandoned.

BACKGROUND OF THE INVENTION

1. Field of the Invention

The present invention relates to recombinant adeno-associated virus vectors for gene delivery and regulated tissue specific expression in at least one mammalian cell such that the expression of the gene is regulated in a tissue specific manner. The present invention also provides a method for using this adeno-associated virus vector for therapeutic purposes.

2. Brief Description of the Prior Art

It is well known that gene therapy of severe hemoglobinopathies requires high level regulated tissue specific expression of a transferred globin gene into hematopoietic stem cells and subsequent high level regulated tissue specific gene expression in maturing erythroid cells. In homozygous patients with such as for example, beta-thalassemia. deficient or absent beta-globin synthesis causes the production of poorly hemoglobinized-defective red cells resulting in severe anemia. Transfer and expression of a normal beta-globin gene, therefore, is highly effective in correcting the defect. In sickle cell anemia, the mutant hemoglobin is susceptible to polymerization resulting in altered red cell rheological and membrane properties leading to vaso-occlusion. An increase in production of one of the globin genes, fetal hemoglobin (hereinafter HbF), appears to ameliorate the severity of sickle cell disease. It will be understood by those skilled in the art that the regulated tissue specific production of normal globin gene products at normal levels in response to environmental stimuli in erythroid cells of a mammalian host with sickle cell anemia is therefore, therapeutic.

It is well known that most strategies for human gene therapy are based on the use of viral vectors for gene transfer. It has been shown that viral vectors capable of infecting virtually every cell in a target population are an efficient method of delivering nucleic acids into mammalian cells. Viral expression vectors have been developed using DNA viruses such as, for example, papovaviruses such as SV40, adenoviruses, herpes viruses, and poxviruses and RNA viruses, such as retroviruses. Generally, the most common used model vectors have been derived from murine and avian retroviruses. These retrovirus vectors utilize packaging cell lines which allow production of replication-defective vectors in the absence of wild-type retroviral helper. The defective retroviral vectors are able to infect and integrate into cells but cannot replicate. The ability to produce helper-free defective retrovirus using packaging cell lines protects against spread of the recombinant virus., and avoids possible dissemination,of recombinant virus-induced disease. It is known to use retroviral vectors to transfer the beta-globin gene into murine hematopoietic stem cells. Although the human beta-globin gene is expressed in most mammals, when transferred into murine hematopoietic stem cells it is only expressed to levels of about 1–2% of the mouse chromosomal beta-globin genes, a level too low to be of any therapeutic value. The disadvantage of the retrovirus packaging lines is that they have been shown to only produce low titers of virus or to produce high levels of wild-type retroviral helper. Another disadvantage is that while the retrovirus vectors can infect a broad class of cell types, cell replication and DNA synthesis are strictly required for provirus integration, therefore restricting efficient use of retroviral based vectors to replicating cells.

The recognition of human retroviruses over the past decade as the etiologic agent of Acquired Immunodeficiency Syndrome (hereinafter AIDS) and in some cases T-cell and hairy cell leukemia have created an awareness of the health risks potentially associated with the use of retrovirus vectors.

It is known by those skilled in the art that retrovirus vectors have resulted in tumors in non-human primate studies as a result of contaminating wild-type retrovirus generated from the packaging cell line. This again points to the unavoidable risk inherent in the retrovirus packaging system.

It is well known that adeno-associated virus (hereinafter AAV) is a human defective, human dependent parvovirus. AAV requires coinfection with another virus such as for example, an adenovirus or certain members of the herpes virus family, for productive infection in cultured cells. In a lytic infection, AAV DNA replicates as a 4.7 kilobase double-stranded molecule and is packaged into virions as linear single-strands of both polarities with no preference as to polarity. It has been shown that in the absence of coinfection with a helper virus, the AAV genome integrates via its termini into the host genome in a site specific manner and resides there in a latent state until the cell is infected with helper virus. When the cell is infected with the helper virus, the AAV DNA is rescued, replicates and establishes a normal productive (lytic) infection.

The single-stranded DNA genome of the human virus AAV-2 (a serotype of AAV) is 4675 base pairs in length and is flanked by inverted terminal repeated sequences of 145 base pairs each. The first 125 nucleotides from a palindromic sequence can form a "T"-shaped hairpin secondary structure and exist in either of two orientations with respect to the genome, designated flip or flop. It has been suggested that AAV replicates according to which the terminal hairpin of AAV is used as a primer for the initiation of DNA replication. It has been shown that the AAV sequences that are required in cis for packaging, integration/rescue, and replication of viral DNA are located within a 191 base pair sequence that includes the terminal repeat sequences. The viral DNA sequence displays two major open reading frames, one in the left half and the other in the right half of the conventional AAV map. At least two regions which, when mutated give rise to phenotypically distinct viruses in the AAV genome. The rep region, which occupies the conventional left half of the genome, encodes proteins that are required for viral replication and for viral rescue when the viral genome is integrated. The cap region which occupies the conventional right half of the genome encodes AAV capsid proteins. Mutants within these three regions are capable of DNA replication but do not produce virus. It is known that AAV contains three transcriptional promoters—p5, p19, and p40. Four rep proteins (rep 78, 68, 52 and 40)

and three capsid proteins (VP-1, VP-2 and VP-3) are derived from alternate splicing of the RNA transcripts of these promoters. These three promoters regulate expression of the genes required for replication and encapsidation of the AAV genome.

It has been shown that the majority of the cis-acting regulatory elements required for regulated tissue specific globin gene expression flank the globin gene cluster or reside within the gene themselves. The majority of these cis-acting regulatory elements have been defined by DNase I hypersensitive sites (hereinafter HS) and are collectively termed the locus control region (hereinafter LCR). Four sites (5' HS I-IV) have been shown to be located several kilobases 5' to the epsilon-globin gene and one site (3' HS VI) has been shown to be mapped 3' to the beta-globin gene. The active elements of the LCR are encompassed within 300–400 base pairs of DNA found at each hypersensitive site and some have been narrowed down to about 30 nucleotides. It is known that the 5' HS II, III and IV when linked to globin genes singly or in combination, substantially enhanced and regulated globin gene expression to a maximum level equivalent to that of endogenous globin genes in transfected erythroleukemia cells or transgenic animals. The past efforts by others to develop retroviral vectors containing globin genes with regulatory elements needed to achieve high level expression have been unsuccessful. These retroviral vectors have been shown to have limited ability to transfer genes that result in regulated tissue specific expression into primate pluripotent hematopoietic stem cells which are a necessary target for genetic therapy of hemoglobin disorders.

Several AAV vector systems have been designed which contain a recombinant plasmid capable of being packaged into AAV particles. These recombinant viruses function as vectors for maintenance or expression of a gene or a DNA sequence in eukaryotic cells when under control of an AAV or SV40 transcriptional promoter.

Hermonat and Muzyczka, 1984, Proc. Natl. Acad. Sci. 81:6466–6470, disclose production of a recombinant AAV (hereinafter rAAV) viral stock in which the neomycin resistant gene (hereinafter neo) was substituted for the AAV capsid region. Hermonat and Muzyczka discloses rAAV transduction of neomycin resistance into murine and human cell lines. Hermonat and Muzyczka state that the stable integrated viral vector can be rescued to produce replicating rAAV sequences after superinfection with adenovirus and wild-type AAV.

Tratschin et al., 1984, Mol. Cell Biol. 4:2072–2081, disclose a rAAV that expresses the chloramphenicol acetyltransferase (hereinafter CAT) gene in human cells under the AAV p40 promoter.

Laface et al., 1988, Virology, 162:483–486, mentions possible gene transfer into hematopoietic progenitor cells mediated by an AAV vector. However, transduction efficiency was extremely low and was determined solely from the number of geneticin-resistant bone marrow colonies. Also, it was possible that this early generation rAAV preparation was contaminated with wild-type AAV virions which decreased rAAV transduction efficiency.

Wondisford et al., 1988, Mol. Endocrinol. 2:32–39, discloses co-transfected cells with two different recombinant AAV vectors each encoding a subunit of human thyrotropin. Wondisford et al. states that expression of biologically active thyrotropin was observed.

In spite of these prior art disclosures, there remains a very real and substantial need for a recombinant adeno-associated virus vector capable of delivering and expressing at least one mammalian gene into a genome of a mammalian host cell such that the expression of the gene is regulated in a tissue specific manner by cis-acting regulating and promoter elements and a method of using the recombinant adeno-associated virus vector for delivering and expressing genes into the cells of a mammalian host in vitro as well as in vivo for therapeutic purposes. More specifically, there is a need for a recombinant adeno-associated virus vector for delivery and expression in a regulated tissue specific manner of globin gene nucleotide sequences and cis-acting elements in erythroid cells of a mammalian host wherein the globin gene is regulated in a tissue specific manner by cis-acting regulatory and promoter elements. There is a need for such vectors capable of transferring coding sequences of a gene under the control of the native genomic transcriptional regulatory elements of that gene for achieving tissue specific, regulated expression of the transferred gene.

SUMMARY OF THE INVENTION

The present invention has met the hereinbefore described needs. The present invention provides a recombinant adeno-associated virus vector capable of delivering and expressing at least one mammalian gene into a genome of a mammalian host cell. The recombinant adeno-associated virus vector of this invention includes at least one mammalian gene, cis-acting regulatory and promoter elements of the gene and an adeno-associated virus such that the expression of the gene is regulated in a tissue specific manner by the cis-acting regulatory and promoter elements. More specifically, the mammalian gene is a human gene wherein the cis-acting regulatory elements are human cis-acting regulatory elements and wherein said promoter elements are human promoter elements.

Another embodiment of this invention provides for the recombinant adeno-associated virus vector of this invention wherein the mammalian gene is a hybrid gene.

A further embodiment of this invention provides for the recombinant adeno-associated virus vector of this invention wherein the cis-acting regulatory and promoter elements are of a globin gene cluster. Preferably, the mammalian gene is a human gene and the cis-acting regulatory and promoter elements are of a human globin gene cluster. This human globin gene cluster includes the cis-acting regulatory and promoter elements located between hypersensitive sites IV and VI.

Another embodiment of this invention provides for the recombinant adeno-associated virus vector of this invention wherein the mammalian gene is a globin gene. More specifically, the globin gene is a hybrid gene.

Another embodiment of this invention provides for the recombinant adeno-associated virus vector of this invention wherein the globin gene is at least one gene selected from the gene cluster group that includes epsilon-globin, $^A$gamma-globin, $^G$gamma-globin, delta-globin, beta-globin and combinations thereof. This globin gene is linked to at least one hypersensitive site wherein the hypersensitive site is located within the globin gene cluster. More specifically, this globin gene is linked to at least one hypersensitive site wherein the hypersensitive site is located within a locus control region.

A specific embodiment of a rAAV vector of the present invention is the rAAV vector, pAAV/HSII $^A\gamma$*/Neo, as depicted in FIG. 1 and disclosed in Example I.

It is within the scope of the present invention to construct various rAAV constructs comprising HS-based promoter/ enhancer fragments fused to the above-mentioned globin genes or gene fragments for transfer to target cell types disclosed throughout this specification.

The present invention is in no way limited to utilizing only rAAV recombinant vectors which comprise HS/globin hybrid constructs for targeting to the appropriate cell type. Instead, the present invention is directed, as noted in the Field of the Invention, to rAAV vectors which are delivered to and expressed in a tissue specific manner within the mammalian host.

To this end, the present invention is also related to non-HS/globin constructs for treating a mammalian host, preferably a human, having a hemoglobinopathy, a blood borne disorder, genetic disease or an acquired disease. This concept is shown in one fashion by the data of Example II, which shows expression of rAAV-β-gal constructs in primary hematopbietic progenitors. A preferred embodiment of this portion of the present invention, included as an example but not a limitation, is the plasmid rAAV/FACC/Neo$^R$, which is utilized to direct phenotypic correction of Fanconi anemia in hematopoietic cells.

A further embodiment of this invention provides for the adeno-associated virus vector of this invention wherein the mammalian host cell includes a bone marrow stem cell and derivatives thereof and an immune cell such as a human hematopoietic stem cell, a human myeloid progenitor cell and a human erythroid progenitor cell. More specifically, the bone marrow stem cell is at least one cell that includes a non-human bone marrow stem cell and a human bone marrow stem cell, and the bone marrow stem cell derivative is at least one cell that includes a derivative of the non-human bone marrow stem cell and a derivative of the human bone marrow stem cell.

Another embodiment of this invention provides a cell product of the recombinant adeno-associated virus vector of this invention.

Further, this invention provides a method of using the recombinant adeno-associated virus vector of this invention that is capable of delivering and expressing in a regulated tissue specific manner at least one mammalian gene into a genome of a mammalian host cell for therapeutic purposes. More specifically, this method includes treating the mammalian host having a hemoglobinopathy, a blood borne disorder, genetic disease or an acquired disease.

Another specific embodiment of the present invention is exemplified by the rAAV vector, JM24/HS432$^A$γ*. Example IV shows efficient transfer, integration and expression of the globin gene expressed by this rAAV vector in primary erythroid cells. This rAAV construct employs the HSIV, HSIII and HSII regions of the LCR discussed within this specification. These rAAV constructs exemplify a running theme of the present invention: rAAV vectors disclosed in the specification are useful in gene therapy applications in general and in treatment of various hemoglobinopathies in particular. The effectiveness of the rAAV vectors of the present invention is limited only by an ability to transfer a rAAV hybrid promoter/gene cassette to the cell type of interest so as to promote tissue specific expression within the target cell, in this case, primary human hematopoietic cells.

To this end, the present invention also relates to non-HS/globin constructs for treating a mammalian host, preferably a human, having a hemoglobinpathy, a blood-borne disorder, genetic disease or acquired disease. A specific and preferred embodiment of this portion of the present invention, included as an example but not as a limitation, is the plasmid rAAV/FACC/Neo$_R$, which is shown in Example III to direct phenotypic correction of Fanconi anemia in hematopoietic cells.

It is also an embodiment of the present invention to treat additional human diseases or disorders by affecting tissue specific expression of rAAV-based therapeutic DNA sequences. As examples, but not forwarded as limitations, the rAAV vectors of the present invention may be utilized for liver specific expression of Factor IX for treatment of hemophilia, expression of CTRF in the lung for treatment of cystic fibrosis, and expression of tyrosine hydrolase in brain tissue for treating Parkinson's disease.

It is an object of the present invention to provide a recombinant adeno-associated virus vector capable of delivering and expressing at least one mammalian gene into a genome of a mammalian host cell for effecting genetic therapy such that the expression of the gene is regulated in a tissue specific manner.

It is an object of the present invention to provide a recombinant adeno-associated virus vector that is capable of delivering and expressing at least one mammalian gene into a genome of a mammalian host wherein the mammalian gene is a hybrid gene, and wherein the expression of this gene is regulated in a tissue specific manner.

It is another object of the present invention to provide a recombinant adeno-associated virus vector that is capable of delivering and expressing at least one human gene into a genome of a mammalian host cell such that the expression is regulated in a tissue specific manner.

It is a further object of the present invention to provide a recombinant adeno-associated virus vector capable of delivering and expressing at least one human globin gene into a genome of a mammalian host such that the expression of the gene is regulated in a tissue specific manner by cis-acting regulator and promoter elements of a human globin gene cluster that includes cis-acting regulatory and promoter elements located between hypersensitive sites IV and VI.

It is an object of the present invention to provide a method for using the recombinant adeno-associated virus vector of this invention for delivering and expressing at least one human gene into a genome of a human host cell for therapeutic purposes such that the expression of the human gene is regulated in a tissue specific manner.

It is a further object of this invention to provide a method for using the recombinant adeno-associated vector of this invention for delivering and expressing at least one globin gene into a genome of a mammalian host cell including employing this method for treating the mammalian host having a hemoglobinopathy, a blood borne disorder, a genetic disease or an acquired disease, in which tissue specific and regulated expression of the delivered gene is desirable.

It is an object of the present invention to utilize the rAAV vector constructs of the present invention to affect therapeutic relief or prophylactic intervention to various human diseases or disorders, both blood-borne and non blood-borne; which are amenable to tissue specific rAAV transduction and target specific expression of a gene or gene fragment which will provide said relief or intervention.

These and other objects of the invention will be more fully understood from the following drawings, description of the invention and the claims appended hereto.

BRIEF DESCRIPTION OF THE DRAWINGS

FIGS. 12A, 12C and 12E are untreated cells. Lymphoblasts from a normal individual: FIGS. 12A and 12B; FA lymphoblasts (BD0215): FIGS. 12C and 12D; rAAV-transduced lymphoblasts: FIGS. 12E and 12F. Data is expressed as number of cells (ordinate) versus DNA content. Raw data are shown with data smoothed by MULTIPLIER. Areas under the curve for G1, S and G2 are shown.

Arrow indicates the predicted molecular weight of the wild-type and mutant FACC polypeptide. The expected sizes of the wild-type and mutant FACC proteins are shown. A GST-FACC fusion protein containing FACC amino acid sequences 281–558, indicated by the hatched region, was used to generate rabbit antiserum. Molecular weight markets are indicated at the right.

Figure 16:
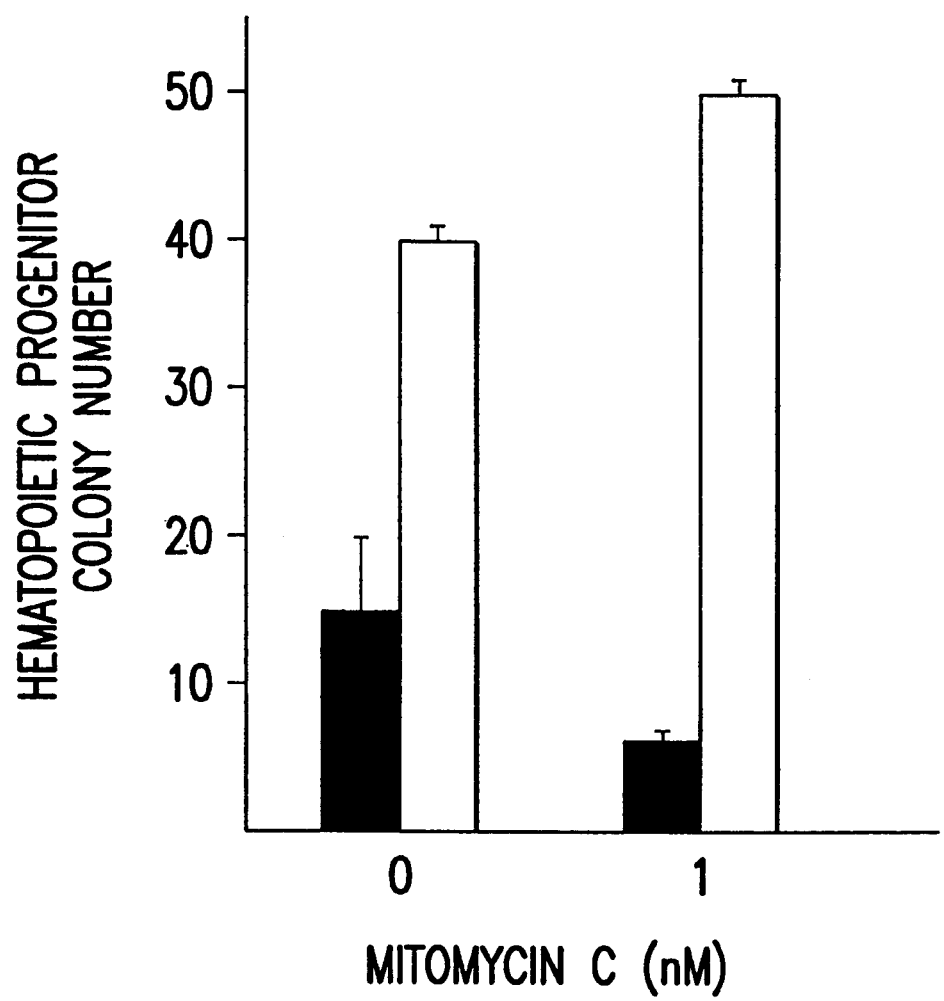

FIG. 16 shows analysis of hematopoietic progenitor colony growth following rAAV/FACC infection of CD34$^+$ cells isolated from a FA(C) patient. The number of progenitor colonies (>50 cells/colony) measured at day 15 in methylcellulose culture following rAAV/FACC virus (▨) or mock infection (■) are shown. Cells were grown in either the absence or presence of 1 nM MMC. Results are expressed as mean colony number ±SEM.

Figure 17:
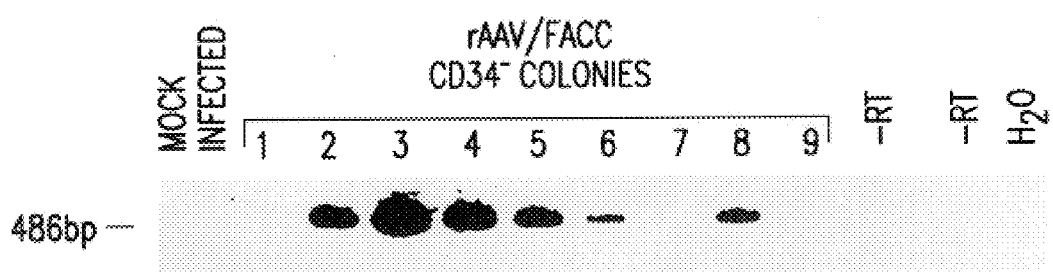

FIG. 17 shows RT-PCR analysis of rAAV/FACC-transduced mRNA expression in hematopoietic progenitor colonies. Total RNAs obtained from apparent MMC-resistant bone marrow colonies were analyzed for rAAV/FACC-specific transcription. RNA isolated from a pool of mock-infected colonies was processed identically to serve as control. Primers specific for the detection of rAAV/FACC transduced expression, the predicted 486-bp fragment, were used. Data from isolated progenitor colonies are shown. RNA from clones processed without reverse transcriptase (RT) and samples without RNA were employed as negative controls.

Figure 18A:
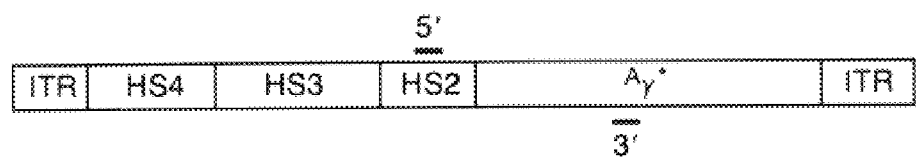
Figure 18B:
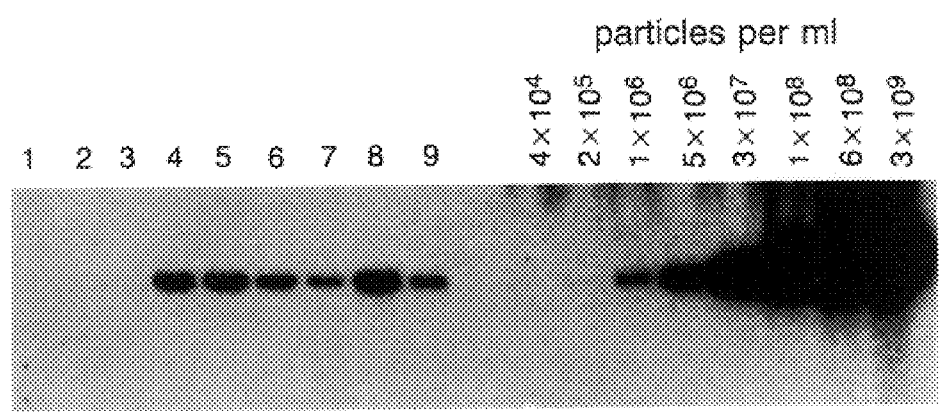
Figure 18C:
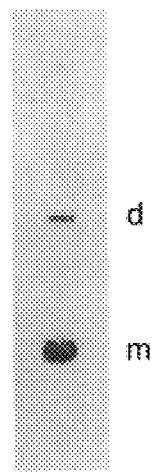

FIGS. 18A–18C show characterization of vHS432$^A\gamma*$. (A) Schematic of the rAAV genome and relative position of the primers used to estimate the particle titer of the cell lysate preparations. The psub201-derived AAV inverted terminal repeats (ITR) flank core regions of the human β-globin LCR: HS4 (GenBank, 958–1714 bp) HS3 (GenBank, 4281–5179 bp) HS2 (GenBank, 8486–8860 bp), and the mutationally marked human $^A\gamma*$ gene. (B) DDP titer of vHS432$^A\gamma*$. Bands represent the 665-bp PCR product spanning the region defined by the 5' and 3' primers shown above. The PCR templates were as follows: lane 1, H$_2$O blank; lane 2, mock adeno-virus-infected cell lysate from cells cotransfected with pAAV/ad and pJM24/HS432$^A\gamma*$; lane 3, vHS432$^A\gamma*$ cell lysate extracted with Stat-60 prior to DNase treatment; lanes 4–6, vHS432$^A\gamma*$ in triplicate; lanes 7–9; vHS2/$^A\gamma*$/neo cell lysate stock (10$^4$ Neo$^R$ per mL) in triplicate. A standard curve generated from pJM24/HS432$^A\gamma*$ DNA of known concentration is shown on the right. (C) Southern blot analysis of Hirt extracted DNA from cells producing vHS432$^A\gamma*$ showing dimer (d) and monomer (m) bands. A 1975-bp fragment (Apa I restriction enzyme fragment of the parent plasmid) containing the $^A\gamma*$ globin gene was used as a probe.

Figure 19A:
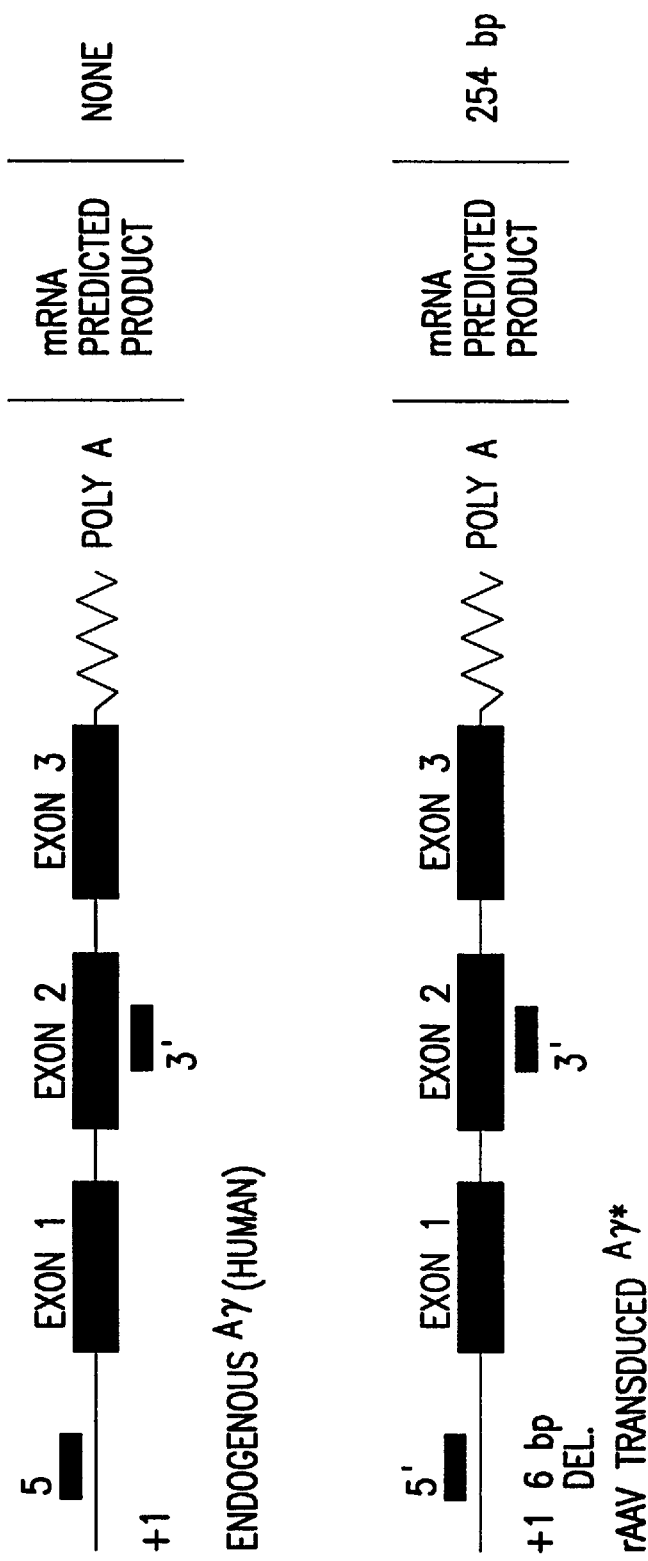
Figure 19B:
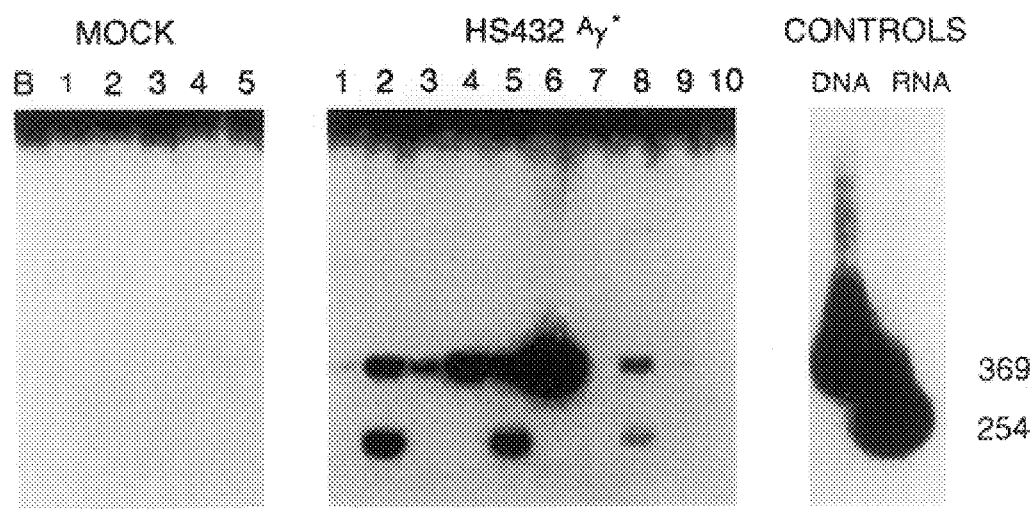
Figure 19C:
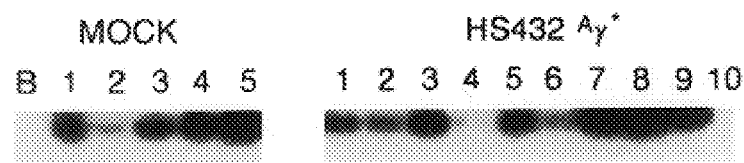

FIGS. 19A–19C show analysis of RNA from colonies derived from human BFU-E transduced with rAAV, vHS432$^A\gamma*$. (A) Schematic of RT-PCR assay showing position of the PCR primers. Primer-template mismatches with the 5' primer that spanned the 6-bp deletion in the $^A\gamma*$ genes prevented efficient amplification of the endogenous gene or mRNA sequences; intron-spanning primers (5', 5'-TCGCTTCTGGAACGTCTATC; 3', 5' CACCTTCTTGCCATGTGCCT) differentiates $^A\gamma*$ DNA and RNA. Conversely, the 5' primer specific for the endogenous gene included nucleotides at its 3' end that are part of the 6-bp deletion in the $^A\gamma*$-globin gene. (B) Analysis of 5 mock and 10 vH432$^A\gamma*$ transduced sickle-cell BFU-E-derived colonies harvested after 14 days in methylcellulose. Lane B is the minus template control. Other controls on the far right show predicted DNA (369 bp) and RNA (254 bp) signals. (C) PCR product derived from 10% of the cDNA template using primers specific for the endogenous γ-globin genes. RT-PCR conditions are given in the text.

Figure 20A:
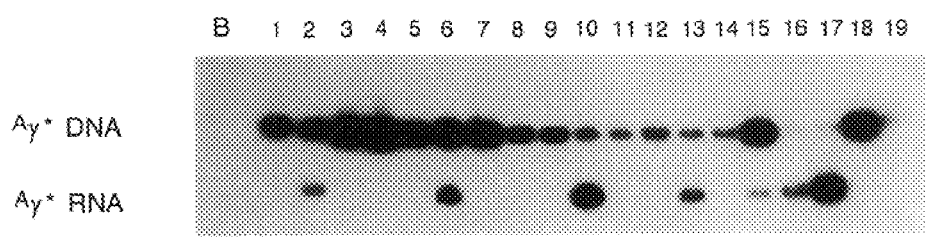
Figure 20B:
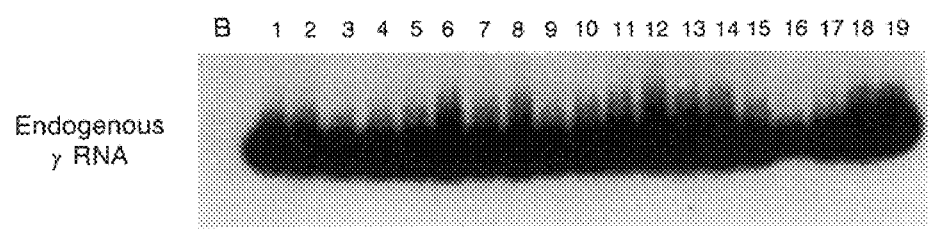
Figure 20C:
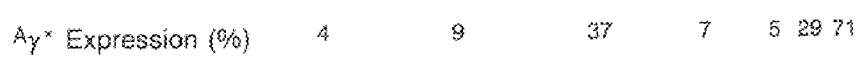

FIGS. 20A–20C show comparison of RT-PCR signals for the transduced the endogenous γ-globin genes. After completion of the RT reaction, the reaction mixture for each individual colony was split into equal volumes and used as matched templates for the primer-specific PCRs. (A) Analysis of 19 sickle-cell BFU-E-derived colonies using the assay and $^A\gamma*$ specific primers shown in FIGS. 2A–2D. Identification of each signal appears on the far left. (B) PCR products using the endogenous γ-globin specific primers. (C) Percent expression from rAAV transduced $^A\gamma*$ gene compared to the γ-globin genes in that colony. Each lane contained an equal volume of the PCR mixture. The gels containing endogenous and $^A\gamma*$ generated signals were then exposed for identical times using a single PhosphorImager screen. Polyacrylamide gel electrophoresis on each sample was performed twice and signals were averaged. The percentages were calculated by multiplying the ratio of the $^A\gamma*$RNA-derived signal intensity and the endogenous γ-globin RNA signal intensity by 100.

Figure 21A:
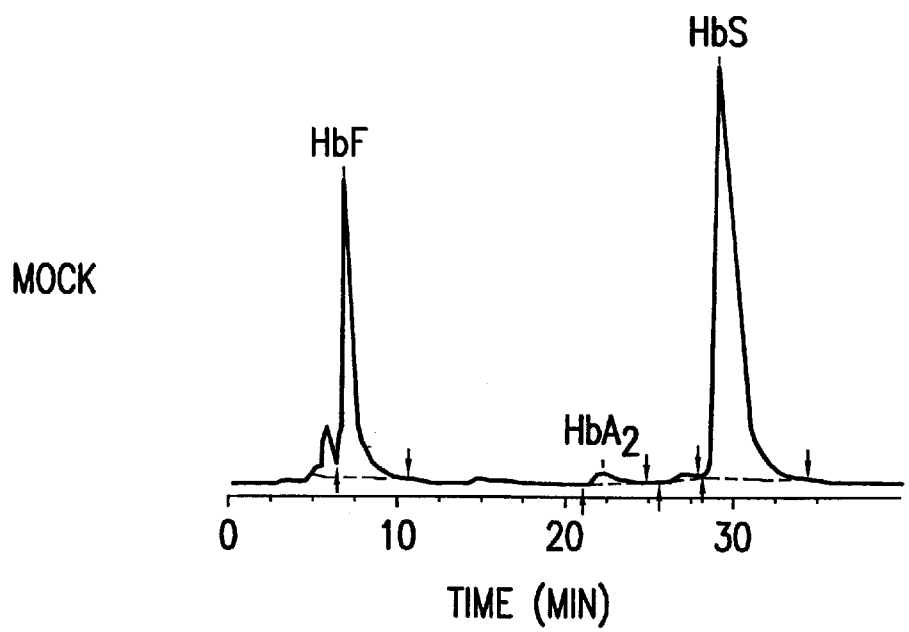
Figure 21B:
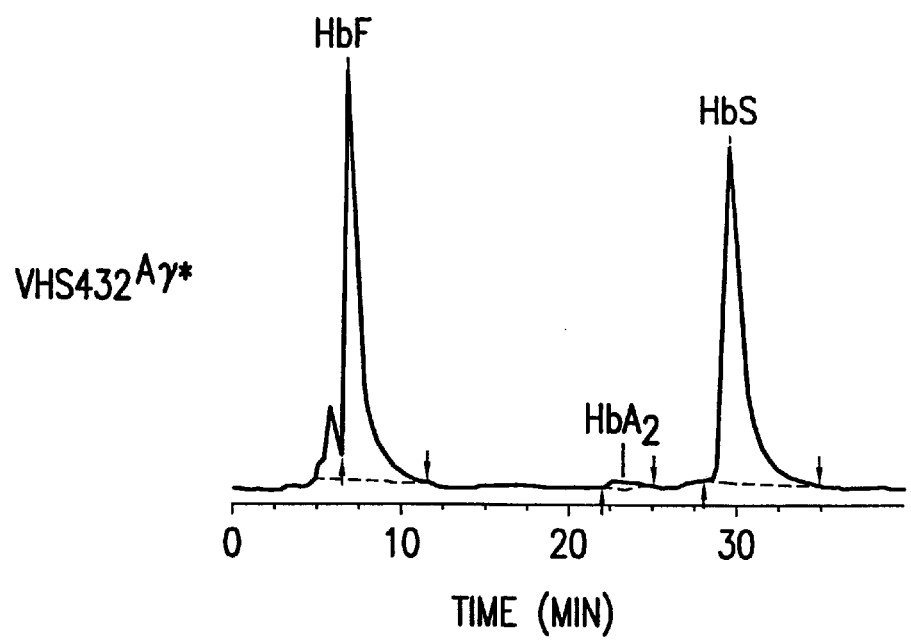

FIGS. 21A and 21B show Hb composition of colonies derived from peripheral blood BFU-E of a patient with sickle-cell anemia. One thousand control (MOCK) or vHS432$^A\gamma*$-transduced cells were plated in methylcellulose. After 19 days, the colonies (>50 erythroid) from the control or experimental plates were pooled, washed and analyzed on cation-exchange HPLC. Major Hb species are identified by their time of elution. The integrated area under each peak provided an estimate of the Hb composition of each pool of colonies. The Hb content was 26% in the control (MOCK) and 40% in the colonies derived from progenitors transduced with vHS432$^A\gamma*$.

It will be understood that the abbreviations set forth in these figures are all standard and well known by those persons skilled in the art.

DESCRIPTION OF THE PREFERRED EMBODIMENTS

As used herein, the term "helper virus" includes a virus such as, for example, adenovirus, herpes virus, cytomegalovirus, Epstein-Barr virus or vaccinia virus, which when coinfected with adeno-associated virus results in productive adeno-associated virus infection of an appropriate eukaryotic cell.

As used herein, the term "mammalian" includes any of the classes of higher vertebrates which is not limited to, for example, humans, and non-human animals.

As used herein, the term "cis-acting regulatory elements" includes any nucleotide sequence that have the ability to increase and decrease transcription of a gene that lies within the same contiguous DNA molecule as the element. The term "cis-acting regulatory elements" includes, but is not limited to, for example enhancer elements, promoters, and repressors.

The term "enhancer elements" include, but is not limited to, for example hypersensitive sites of a gene cluster and hypersensitive sites of a locus control region.

The present invention provides a recombinant adeno-associated virus vector capable of delivering and expressing at least one mammalian gene into a genome of a mammalian host cell. This recombinant adeno-associated virus vector includes a mammalian gene, cis-acting regulatory and promoter elements of the gene, and an adeno-associated virus. The expression of this gene is regulated in a tissue specific manner by the cis-acting regulatory and promoter elements.

Preferably, the mammalian gene is a human gene wherein the cis-acting regulatory elements are human cis-acting regulatory elements and wherein the promoter elements are human promoter elements.

The present invention provides a recombinant adeno-associated virus vector as hereinbefore described wherein the mammalian gene is a hybrid gene. This hybrid gene is a gene having at least one nucleotide sequence selected from the group consisting of a human nucleotide sequence, a non-human nucleotide sequence, a synthetically derived nucleotide sequence and combinations thereof.

It will be appreciated by those skilled in the art that the hybrid genes of this invention exist because of codon degeneracy and evolutionary protein conservation. It is understood by those skilled in the art that due to codon degeneracy, more than one trinucleotide DNA sequence can code for different amino acids. It is well known that sixty-one triplets correspond to particular amino acids, and that three code for chain termination. Because there are twenty amino acids and sixty-one triplets that code for them, it is understood by those skilled in the art that the genetic code is highly degenerate. This degeneracy account for the fact that many amino acids are designated by more than one triplet. Thus, it is possible to change the coding sequences to synthesize DNA sequence to code for exactly the same peptide. Also, it is well known by those skilled in the art that certain proteins have varying degrees of conservation from one species to the other. It will be understood that proteins can have varying degrees of divergence from each other in terms of their amino acid and nucleotide sequence while still retaining exactly the same function. These proteins can replace or act concomitantly with proteins of the same family in different species, such as for example, the ability of human globin to act in a mouse background.

In another embodiment of this invention, a recombinant adeno-associated virus vector, as herein described, is provided wherein the cis-acting regulatory and promoter elements are of a globin gene-cluster. Preferably, the mammalian gene is a human gene and the cis-acting regulatory and promoter elements are of a human globin gene cluster. The human globin gene cluster includes cis-acting regulatory and promoter elements located between hypersensitive sites IV and VI. Hypersensitive site IV is located about 18 kilobase pairs 5' to an epsilon-globin gene (∈-globin gene), and hypersensitive site VI is located about 21.8 kilobase pairs 3' to the epsilon-globin gene.

In another embodiment of this invention, arecombinant adeno-associated virus vector as hereinbefore described is provided wherein the mammalian gene is a globin gene. More specifically, this invention provides the recombinant adeno-associated virus vector as hereinbefore described wherein the globin gene is a human globin gene and wherein the cis-acting regulatory and promoter elements are of the human globin gene, Another embodiment of this invention provides a recombinant adeno-associated virus vector, as hereinbefore described, wherein the globin gene is at least one gene selected from the gene cluster group consisting of epsilon-globin (∈-globin), $^A$gamma globin ($^A\gamma$ globin), $^G$gamma globin ($^G\gamma$ globin), delta-globin (δ-globin) and combinations thereof. More specifically, the globin gene is linked to at least one hypersensitive site, wherein the hypersensitive site is located within the globin gene cluster. Preferably, the globin gene is linked to at least one hypersensitive site which is located within a locus control region.

A further embodiment of this invention includes a recombinant adeno-associated virus vector as hereinbefore described wherein the mammalian host cell is at least one cell selected from the group consisting of bone marrow stem cell a bone marrow stem cell derivative, a hematopoietic stem cell, a human myeloid progenitor cell and a human erythroid progenitor cell. The bone marrow stem cell is at least one cell selected from the group consisting of (a) a non-human bone marrow stem cell and (b) a human bone marrow stem cell. The bone marrow stem cell derivative is at least one cell selected from the group consisting of (a) a derivative of the non-human bone marrow stem cell and (b) a derivative of the human bone marrow stem cell.

In another embodiment of this invention a cell product of the recombinant adeno-associated virus vector as hereinbefore described is provided.

In yet another embodiment of this invention, a method of using a recombinant adeno-associated virus vector characterized by being capable of delivering and expressing in a regulated tissue specific manner at least one mammalian gene into a genome of a mammalian host cell for a therapeutic purpose is provided that includes introducing the recombinant adeno-associated virus vector having the mammalian gene, cis-acting regulatory and promoter element of the gene, and an adeno-associated virus wherein the gene is regulated in a tissue specific manner, into the mammalian host cell for effecting the therapeutic purpose.

More specifically, this method includes employing this method using the recombinant adeno-associated virus vector as hereinbefore described for treating a mammalian host having, for example, a hemoglobinopathy, a blood borne disorder, a genetic disease, or an acquired disease in which tissue specific and regulated expression of the delivered gene is desirable. The hemoglobinopathy includes, but is not limited to, for example, sickle cell disease or β-thalassemia. The blood borne disorder includes, but is not limited to, for example, Gaucher's disease.

Table I sets forth corrected copy expression, as determined by densitometry, of RNA expression of recombinant adeno-associated virus/K562 clones of this invention.

TABLE I

| RNA EXPRESSION OF rAAV/K562 CLONES | | |
|---|---|---|
| | % Expression | |
| Clone | Uninduced | Induced |
| 1 | 60 | 100 |
| 2 | 25 | 40 |
| 3 | 30 | 60 |
| 4 | 50 | 100 |
| 5 | 40 | 110 |
| 6 | 45 | 80 |
| 7 | 45 | 60 |
| Polyclonal | 40 | 85 |

$$\% = \frac{\text{Transduced g-Globin RNA}}{\text{Endogenous g-Globin RNA}} \times \frac{6 \text{ Endogenous Genes}}{\text{Copy Number}}$$

Using a correction for the chromosomal gene copy number (six copies), Table I shows the relative expression of the transferred gene compared to the endogenous genes. Table I shows that in every case, the transferred $^G\gamma$-globin gene exhibited increased expression after hemin induction that paralleled that of the native chromosomal globin genes. Table I shows that in uninduced cells, the transferred gene was expressed at about 40 to 50 percent of the level of a single chromosomal gene. This proportion increased to an average of about 85 percent of the level of a single chromosomal gene after hemin induction.

Quantitation of RNA message by PCR was comparable to that determined by RNase protection and confirmed high level expression of the transduced $^A\gamma$ gene including induction by hemin. S1 primer extension experiments confirmed that the correct globin start site was used in the proviral state. To rule out the possibility, that the regulated globin expression observed with this construct was due to globin regulatory sequences (LCR 2) and not Viral sequences or chromosomal positioning, an AAV/globin hybrid virus identical to the one described above minus the LCR 2 site was constructed Similar characterization of these transduced genes indicated a marked reduction in globin expression as expected, (i.e., (the construct is unresponsive to hemin induction).

The data of Table I demonstrates that this invention is the first viral-base introduction in which correct levels and regulation of gamma globin gene expression is achieved in an erythroid derived cell line. High level, regulated globin expression was obtained when using a construct containing the cis-acting locus control region LCR site 2. The LCR/globin construct efficiently integrated into the genome without rearrangement in all clones studied. Moreover the messenger RNA expression of the transduced gene was comparable to endogenous gamma globin levels. The correct globin start site was utilized in the transduced gene and tissue specific expression which was hemin inducible was maintained.

Figure 1A:
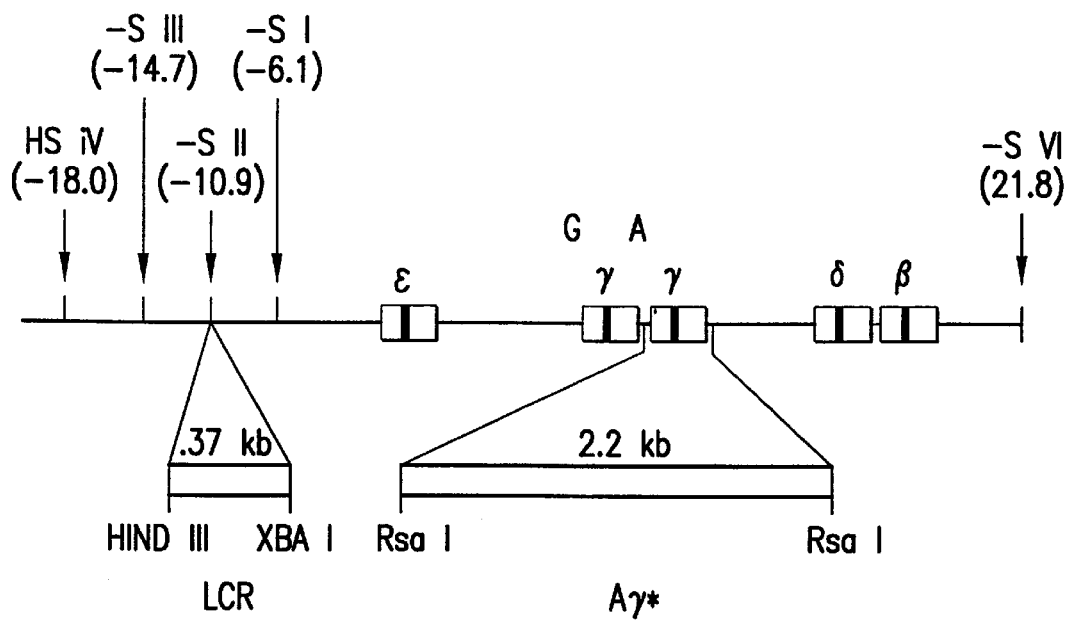
FIG. 1A shows a schematic representation of the human globin cluster.
Figure 1B:
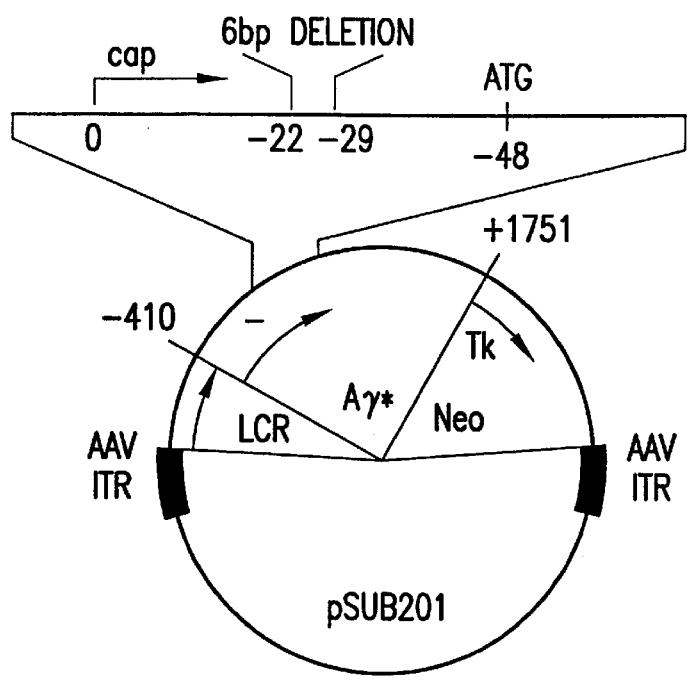
FIG. 1B shows the construction of a specific rAAV vector of the present invention.

FIGS. 1A and 1B generally show the restriction endonuclease cleavage map for the recombinant adeno-associated virus vector of this invention having a marked gamma globin gene linked to a 400 nucleotide Hind III/XbaI fragment of the cis-acting LCR-site 2. This fragment was cloned into the AAV vector psub201 using standard DNA techniques well known by those skilled in the art. All fragments were subcloned in the same 5' to 3' orientation.

FIG. 1A shows the schematic representation of the human beta-globin gene cluster. The five functional genes of this cluster—epsilon-globin (∈), $^G$gamma globin ($^G\gamma$), $^A$gamma globin ($^A\gamma$), delta-globin (δ), and beta-globin (β) are indicated by the boxes. The arrows shown in FIG. 1A show the location of the five major DNase I HS at distances in kilobase pairs from the epsilon-globin gene. FIG. 1A also shows the HS2 fragment and the $^A$gamma globin gene used in the construction of the vector of this invention.

FIG. 1B shows the HS2 fragment marked $^A$gamma globin gene with 6 base pairs deleted at +23 to +28 relative to the cap site, and Neo$^R$ gene were subcloned into psub201 (Samulski).

The ability of adeno-associated virus (AAV) to infect primary hematopoietic stem cells determines its applicability to human gene therapy. Transduction frequencies of about 50 to 80 percent have been achieved in tissue culture cells using recombinant vectors lacking the replication functions that are free of helper virus. Infection of primary mouse hematopoietic progenitors by using generation vectors that retained the replication function are known by those skilled in the art. (See Laface et al., 1988 Virology 162:483–486 (1988)).

The present invention sets forth that the recombinant adeno-associated virus vectors of this application are used effectively for the transfer of globin genes, for example, into human cells, and more specifically that the adeno-associated virus globin vectors of this invention may be employed for transferring genes into primary hematopoietic cells.

Another specific embodiment of the present invention is exemplified by the rAAV vector, JM24/HS432$^A\gamma$*. Example IV shows efficient transfer, integration and expression of the $^A\gamma$-globin gene encoded by JM24/HS432$^A\gamma$* and expressed in primary euthyroid cells. These data show the versatility of the rAAV vectors of the present invention to promote tissue specific expression within the target cell, in this example a primary human hematopoietic cell. These data also show the ability of an rAAV vector of the present invention to introduce, integrate and express a gene or gene fragment into a primary human hematopoietic cell without initial selection in the presence of an antibiotic.

Additionally, the present invention is in no way limited to utilizing the rAAV vectors of the present invention only in gene therapy of various hemoglobinopathies disclosed within this specification. It is also an embodiment of the present invention to treat various additional human diseases or disorders by affecting tissue-specific expression of rAAV-based therapeutic DNA sequences. As examples, but not forwarded as a limitation, rAAV vectors of the present invention may be utilized for liver specific expression of Factor IX for treatment of hemophilia, expression of CTRF in lung tissue for treatment of cystic fibrosis, and expression of tyrosine hydrolase in brain tissue for treating Parkinson's disease.

A specific embodiment of the present invention involves gene therapy of hemorrhagic diseases related to abnormalities in clotting factors, specifically treatment of factor IX deficiency, also known at Christmas disease, or Hemophilia B, is exemplified with rAAV vectors of the present invention. Severe Factor IX deficiency is a disorder clinically indistinguishable from Factor VIII-involved Hemophilia A. Both clotting factors are expressed primarily in the liver in the absence of liver disease. Factor IX deficiency is inherited as an X-linked recessive trait and my occur asymptomatically or with associated hemorrhage.

Therefore, it is within the scope of the present invention to construct a rAAV vector housing a hybrid gene wherein any liver specific promoter is fused directly upstream of the Factor IX coding region.

Liver cells (HepG2: a hepatocellular carcinoma cell line derived from a human male) are infected with either mock virus (control), an adenovirus vector carrying a liver specific promoter and therapeutic gene, or an rAAV vector carrying this gene cassette. It can be shown that both the an adenovirus vector and rAAV vector comprising the hybrid construct express human Factor IX in liver cells, but not in non-liver cells. This example shows that use of the rAAV vectors of the present invention are not to be limited to tissue-specific expressions of globin genes. Instead, various other cell types (such as liver cells) may be targeted with the rAAV-based constructs of the present invention. The skilled artisan is limited only in the ability to find an appropriate cis-acting regulatory element to confer proper expression within the target cell, Additionally, the skilled artisan may review Example III of this specification for another example of rAAV-based expression of a therapeutic protein. The Rous Sarcoma Virus (RVS) promoter was fused to the FACC cDNA coding region, subcloned into an rAAV vectors and utilized to correct the phenotypic deficiency associated with Fanconi anemia. It is evident the present invention encompasses use of known eukaryotic promoters and/or enhancer sequences which will promote expression of the gene or gene fragment of interest within the transduced target cell.

In order to provide greater detail of this invention, the following examples are provided.

EXAMPLE I

It is well known that the construction of AAV hybrid vectors requires transient introduction and expression of an AAV helper plasmid with the recombinant AAV vector plasmid in adenovirus infected human cells.

The following example characterizes AAV as a vector for globin delivery in culture erythroid cells. The prior art has identified cell types and species of origin that have successfully been transduced by AAV vectors include: (1) Human; HeLa (human cervical carcinoma), Detroit 6 (human lung fibroblast), KB (epidermoid carcinoma), K562 (chronic myelogenous leukemia line), NC37 (normal lymphoblastoid line), KGla, HEL, HL60, and U937 (four myeloid leukemia lines), human erythroid progenitors cells; (2) monkey; CV1 and BSC40 (kidney derived lines); (3) mouse; BKLKCL4 (primary skin fibroblast), NIH 3T3 (mouse embryo), L-M TK- (mouse fibroblast), and murine hematopoietic progenitor cells. In each prior art case the vector promoter has been of viral origin (SV40 or AAV). Although these prior art examples verify that numerous cell types from different species are susceptible to infection by AAV vectors, little is known about tissue specific expression by nonviral general or tissue specific promoters within the AAV genome. In the case of retroviral vectors, the upstream LTR promoter can interfere with expression of downstream internal promoters. To avoid problems of promoter interference some recent retroviral vectors are devoid of their own promoter and enhancer sequences. In the case of AAV, the terminal repeats of the vector are not known to contain an promoter activity, but the effect of AAV sequences on internal promoters has not been examined experimentally.

To test the recombinant AAV vector of this invention for the efficient transduction and expression of globin gene sequences in the erythroid cell line K562, we constructed a recombinant-AAV (rAAV) vector containing the human $^A$gamma globin gene, marked with a 6nt deletion in the 5' untranslated region to allow its transcript to be distinguished from native gamma globin transcripts. The globin gene was linked to a 400 nucleotide DNA fragment containing LCR site 2, and a bacterial neomycin-resistance gene used for selection. Site 2 alone has been shown to confer high level globin gene expression in erythroleukemic K562 cells and transgenic mice. When treated with hemin, K562 cells can be induced to differentiate, which results in increased expression of epsilon and gamma globin genes. K562 cells were infected with the recombinant AAV/globin virus, and neo$^R$ cells obtained. Both a polyclonal and a pool of twenty individually isolated clones were studied.

Figure 2A:
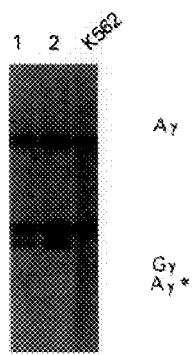
FIG. 2A shows a Southern Blot analysis of DNA from K562 cells infected with recombinant adeno-associated virus containing the HS2 fragment (rAAV/HS2/$^A$gamma globin/Neo).
Figure 2B:
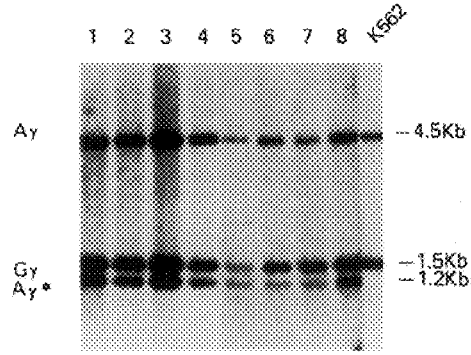
FIG. 2B shows a Southern Blot analysis of individual clones infected with rAAV/HS2/$^A$gamma globin/Neo.

FIGS. 2A and 2B show the Southern Blot analysis of rAAV/K562 pooled and individual clones, respectively.

FIG. 2A shows the Southern Blot analysis of two pools (rAAV/K562 pools) of 30 individual clones of cells infected with recombinant AAV containing the HS2 fragment (rAAV/HS2/$^A$gamma globin/Neo). DNA was digested with PvuII. FIG. 2A shows bands containing the endogenous $^A$gamma globin signal that migrates at 4.5 kb and that $^G$gamma globin migrates at 1.5 kb. The expected 1.2 kb band represents the HS2 containing construct using an XhoI/PvuII $^A$gamma globin probe. K562 mock-infected cells served as a source of control DNA. These Southern Blot analyses revealed a single unrearranged copy/cell of the transferred globin gene linked to site 2 demonstrating the stability of the transduced gene. The basal and hemin induced expression of the transduced gene was equivalent to that of a single native globin gene. When assuming that all endogenous copies of globin were expressed, we measured uninduced expression of the marked gene to be 70% that of a single endogenous gene which, with hemin induction, rose to 100%. Several non-erythroid tissue culture lines were examined for evidence of gamma globin transcripts. A small (1–5% of rAAV/K562 signal) but detectable signal was found in Detroit 6 and HeLa cells but not in T lymphoid CEM cells. This clearly demonstrates tissue specific expression of this construct.

FIG. 2B shows Southern Blot analysis of individual clones infected with rAAV/HS2/$^A$gamma globin/Neo. After densitometric analysis, the proviral copy number was calculated by multiplying the signal ratio of transduced $^A$gamma globin/Neo endogenous gamma globin by 3.

Figure 2C:
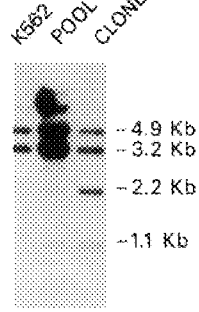
FIG. 2C shows a Southern Blot analysis of a pool of 30 clones and a single clone generated by infection of K562 cells with the recombinant virus lacking the HS2 fragment (rAAV/$^A$gamma globin/Neo).

FIG. 2C shows the Southern Blot analysis of a pool of 30 clones and a single clone generated by infection of K562 cells with the recombinant virus lacking the HS2 fragment (rAAV/$^A$gamma globin/Neo). DNA was digested with XbaI. FIG. 2C shows bands containing the endogenous $^A$gamma globin and $^G$gamma globin genes that migrate at about 4.9 and 3.2 kilobase pairs respectively. The expected 1.1 and 2.2 kilobase bands are derived from the construct lacking HS2 after genomic digests with PvuII. Genomic DNA was isolated, digested with PvuII and electrophoresed on 0.8% agarose gel. Using ammonia acetate transfer, the digested DNA was transferred to Hybond-n$^+$ (Amersham, Arlington Heights, Ill.) and probed with a XhoI/PvuII (840 nt) $^{32}$P-labelled fragment of the gamma globin gene. Filters were washed to a final stringency of 2xSSC (standard saline citrate) at about 65° C. for about 1 hour.

S1 primer extension experiments confirmed that the correct globin start site was used in the proviral state. To rule out the possibility that the regulated globin expression we observed with this construct was due to globin regulatory sequences (LCR 2), and not viral sequences or chromosomal positioning, we constructed an AAV/globin hybrid virus X,identical to the one described above minus the LCR-2 site. Similar characterization of these transduced genes indicated a marked reduction in globin expression as expected demonstrating the tissue specific regulation of the construct of the invention.

Figure 2D:
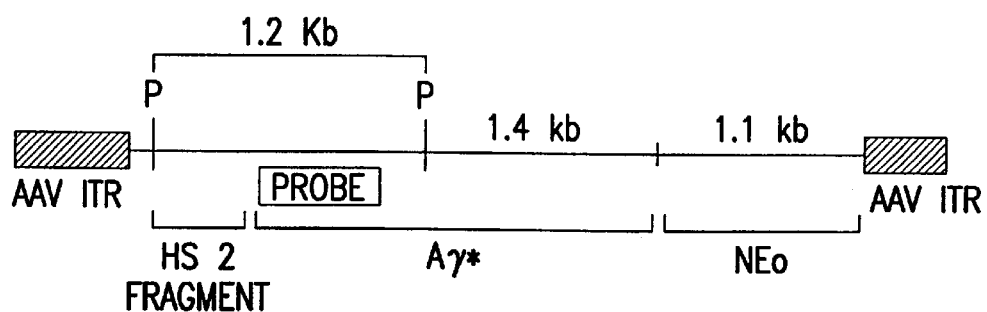
FIG. 2D shows the construct of the expected 1.2 kilobase pair size fragment after genomic digests.

FIG. 2D sets forth the construct that shows the expected 1.2 kilobase pair size fragment after genomic digests with Pvu II.

Figure 3A:
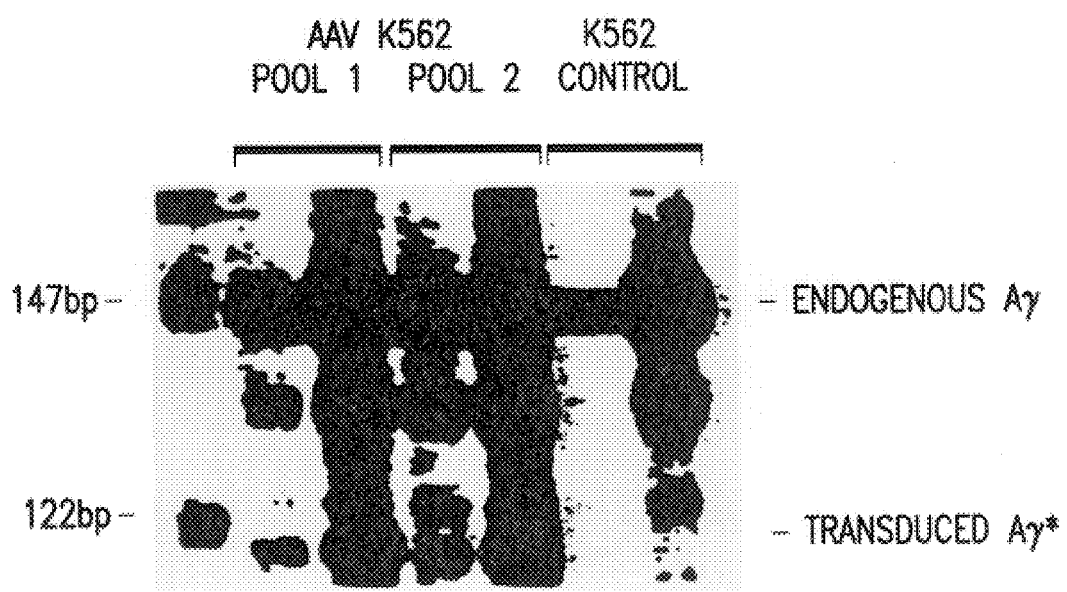
FIGS. 3A and 3B show a RNase protection assay of RNA extracted from K562 cells infected with rAAV/HS2/$^A$gamma globin/Neo or rAAV/$^A$gamma globin/Neo.
Figure 3B:
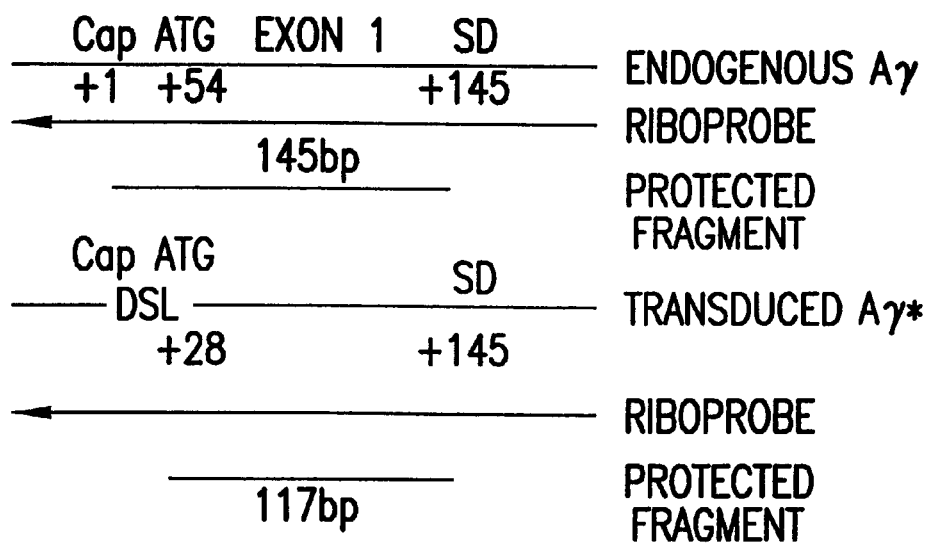

FIGS. 3A and 3B show the RNase protection assay of rAAV/K562 pooled clones. Predicted protected fragments were 145 nt for the endogenous gamma globin genes ($^A$γ and $^G$γ) and 117 nt for the marked transduced gene. rAAV/K562 clones were pooled and 20 hg of cytoplasmic RNA was assayed as previously described mock type Agamma globin gene. (See Sorrentino et al., 1990, Nucleic Acids Research 18:2721–2731).

These results represent the first viral-based introduction in which correct levels and regulation of gamma globin gene expression was achieved in an erythroid derived cell line. High level, regulated globin expression was obtained and efficient integration into the genome without rearrangement occurred in all clones studied. Moreover the messenger RNA expression of the transduced gene was comparable to endogenous gamma globin levels. The correct globin start site was utilized in the transduced gene and tissue specific expression which was hemin inducible was maintained. This suggests that recombinant AAV vectors can be used effectively for the transfer of globin genes under their own regulation into human cells. It will be understood by those persons skilled in the art that the recombinant AAV vectors of this invention can be used to achieve tissue-specific regulated expression of the coding sequences of a gene under the control of that gene's transcriptional elements. Such vectors are useful for treatment of hemoglobinopathies, blood borne diseases, and genetic or acquired diseases in which tissue-specific and regulated expression of the transferred gene is required. Among such disorders are the severe beta-thalassemias and sickle cell anemia in which high level expression of a globin gene in erythroid cells is necessary. Another example is Gaucher's disease in which production of glucocerebrosidase in macrophages is desired. Many metabolic disorders require liver-specific gene expression. Among these are familial hypercholesterolemia in which expression of the LDL receptor is desired.

EXAMPLE II

One of the specific embodiments of the present invention is directed gene transfer to hematopoietic stem cells to treat a variety of blood-borne diseases or disorders. To this end, the present example shows gene transfer into a primary hematopoietic progenitors. This example shows that hematopoietic progenitor cells are infected with high efficiency with rAAV-based vectors.

A rAAV vector containing the β-galactosidase (β-gal) gene was used in order to assay for transduction and gene expression in cell monolayers or in single-cell suspensions. Semiquantitative polymerase chain reaction (PCR) analysis was used to evaluate DNA from progenitor-derived colonies for evidence of gene transfer. Site preferred integration into chromosome 19, a feature of latent infection with wild-type AAV, is not generally observed with rAAV. Therefore, wild-type AAV is utilized in the present example to evaluate integration in primary hematopoietic cells.

1. Materials and Methods

Viruses and cells—Wild-type human adenovirus 5 (Ad5) was obtained from the American Type Culture Collection (ATCC), Rockville, Md. The human bladder carcinoma cell line, 5637, was also obtained from the ATCC. Detroit 6, 293, and K562 cells were maintained in Dulbecco's modified Eagle's medium (DMEM) containing 10% fetal calf serum (FCS), 2 mmol/L glutamine, 100 U/mL penicillin, and 0.1 mg/mL streptomycin. A cell line containing a single integrated copy of the (β-gal) gene as part of a proviral genome (G1BgSVNa-clone 29), obtained from Genetic Therapy (Gaithersburg, Md.), was maintained in the same medium. 5637 cells were maintained in RPMI 1640 containing 10% FCS, 2 mmol/L glutamine, 100 U/ml penicillin, and 0.1 mg/mL streptomycin, and the 5637 cell-conditioned media was harvested after 7 days.

Figure 9:
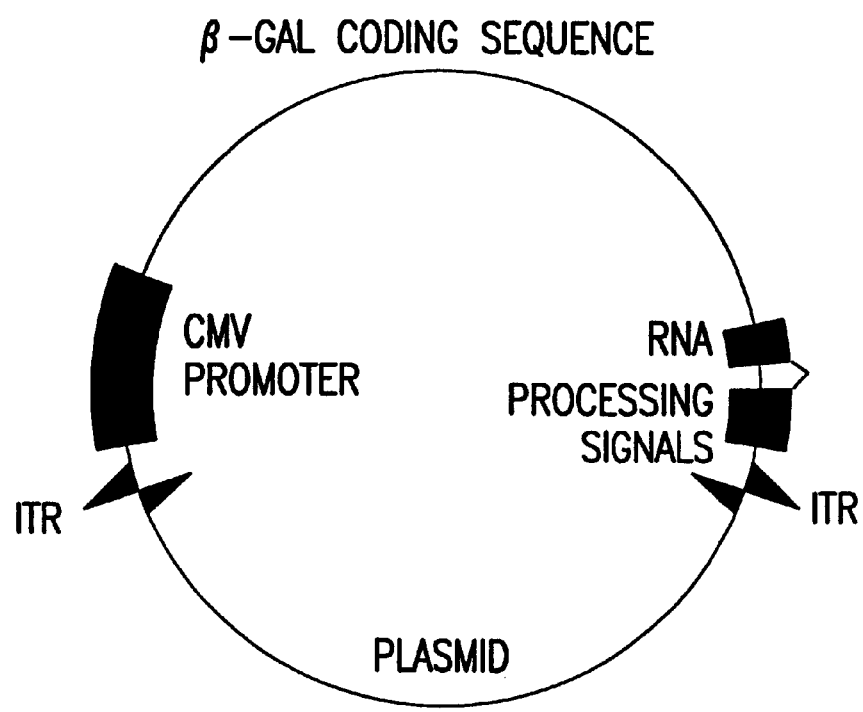
FIG. 9 shows the general organization of the β-gal vector in plasmid form. The CMV E1-A promoter was linked to the β-gal coding sequences followed by mP-1 RNA processing signals. This entire cassette is flanked by the AAV inverted terminal repeats (ITR). This plasmid was constructed as described in the Example II.

Construction of the rAAV-β-Gal vector—The plasmid pnLacF containing the coding sequences for LacZ(β-gal), modified to incorporate a eukaryotic translation initiation codon, an N-terminal nuclear localization signal, and the RNA-processing signals from the mouse protamine-1 (mP-1) gene, was obtained from Jacques Pershon (Immunex Co. Seattle, Wash.). The CMV E1-A promoter within an XhoI-PstI fragment was inserted as a blunted fragment into a blunted XbaI site 5' to the LacZ coding sequences. The entire cassette containing the CMV promoter, β-gal coding sequences, and mP-1 RNA-processing signals was inserted between the NsiI-SnaBI sites of pDX11 to create the plasmid pAB-11 (FIG. 9). pDX11 was derived by subcloning the rAAV genome from pd 113–94 into the PstI site of pGEM3A (Promega, Madison, Wis.).

Generation of AAV and rAAV vectors—AAV type 2 was obtained from ATCC, and maintained by infecting either 293 or HeLa cells; helper function was provided by Ad5 strain dl309 (T. Shenk, Princeton University), used a multiplicity of infection (MOI) of 10. At 48 hours post infection, the cells were collected with the medium, frozen and thawed three times. After low-speed centrifugation, the cell lysate containing wild-type AAV was heated to 55° C. for 1 hour to inactivate the adenovirus, aliquoted and stored at −20° C. for use. The titer of the AAV virus stock was determined indirectly either by immunostaining of infected cells with anticapsid antibodies or by quantitative Southern blot analysis. For preparation of rAAV, 60% to 80% confluent 293 cells were infected with adeno-virus type 5 at an MOI of 5 to 10 as described by Samulski, et al (1989, J. Virol. 63: 3822). rAAV viral stocks were generated by subsequent calcium phosphate contransfection of 10 μg of plasmid pAB11 and 10 μg helper plasmid (pAAV/Ad) 2 to 4 hours after adenoviral infection. Cells were harvested 48 to 72 hours posttransfection, frozen and thawed four times, and centrifuged to remove debris. Inactivation of adenovirus was achieved by heating to 55° C. for 30 minutes. Heating of the viral preparations eliminated infectious adenovirus, as no cytopathic effect was observed over 7 to 10 days after exposure of 293 or Detroit 6 cells to lysate diluted 1:1. For some preparations, in an effort to achieve a high viral titer, the plasmid DNA was introduced by lipofection using liposomes prepared according to protocols provided by the vendor, GIBCO (Grand Island N.Y.). For these preparations, the cells were lysed by sonication in DMEM-10% FCS or phosphate-buffered saline (PBS), clarified by centrifugation, and stored at 4° C.

Histochemical staining for β-Gal activity—Aliquots of lysates (0.01 mL to 0.1 mL) were added to Detroit 6 cells at 60% to 80% confluency and allowed to incubate for 18 hours. Plates were washed, fixed with 2% formaldehyde and 0.2% glutaraldehyde for 5 minutes at 4° C., and stained for X-gal for 36 hours as described by Janes, et al. (1986, EMBO J 5: 3133). The cells were washed three times in PBS and enzyme reaction developed in PBS containing 1 mg/mL of X-gal, 2 mmol/L $MgCl_2$, 5 mmol/L potassium ferrocyanide, and 5 mmol/L potassium ferrocyanide at 37° C. for 24 to 36 hours. The cells were then washed in PBS. Cytospin preparations of suspension cells were processed identically after fixation for some experiments. Individual blue nuclei were counted to estimate the viral titer. For processing of fresh cells, 150 μg of X-gal!mL was added to the culture medium and the incubation continued at 37° C. in 5% $CO_2$ for 16 hours. Cytospin preparations were prepared using standard techniques.

Purification of human and rhesus bone marrow progenitors—Human bone marrow cells were obtained from normal volunteers after informed consent using a study protocol approved by the National Heart Lung and Blood Institute Review Board. Bone marrow aspirates were obtained by standard clinical techniques. Low-density mononuclear cells were isolated by buoyant-density centrifugation (Ficoll-Hypaque), and $CD34^+$ cells were recovered by positive immunoselection using an avidin-biotin-conjugated column system (Ceprate LC) according to the manufacturer's instructions (Cell-Pro, Bothell, Wash.). Purity was estimated by flow cytometric analysis of the immunoselected $CD34^+$ cell population after restaining with an anti-CD34 antibody or mouse antihuman IgG2a (isotypic control) conjugated to phycoerythrin. Sixty percent of 90% of the recovered cells were $CD34^+$. In addition, the starting mononuclear cell population and immunoselected $CD34^+$ cells were plated in clonogenic cultures in methylcellulose using standard conditions. A 57 to 90-bold enrichment in colony-forming progenitors was achieved.

Rhesus bone marrow cells were obtained by aspiration and a mononuclear cell preparation prepared by buoyant-density centrifugation; CD34 selection was performed using an antibody (K6.1) that reacts with rhesus CD34 antigen. A 12 to 94-fold enrichment was achieved, as reflected by the concentration of clonogenic progenitors in the staring mononuclear versus of the immunoselected cell population.

Infection and culture of enriched progenitors—CD34$^+$ immunoselected cells were incubated in suspension culture containing DMEM with 10% to 15% FCS, 2 mmol/L glutamine, 100 U/mL penicillin, 0.1 mg/mL streptomycin, 10 ng/mL interieukin (IL)-3, 50 ng/mL IL-6 and 100 ng/mL stem-cell factor (SCF). The cultures were exposed to no virus, wild-type AAV, or rAAV for 1 to 96 hours, at which time cells were harvested washed, and aliquoted for morphologic analysis (cytoprep), methylcellulose assay, and in some instances, β-gal activity analysis.

Human bone marrow mononuclear cells.($10^5$/mL) and CD34$^+$ immunoselected cells ($10^3$/mL) were plated in Iscove's methylcellulose medium (Terry Fox Laboratories, Vancouver, Canada) consisting of Iscove's media, 0.8% methyl cellulose, 30% FCS, 1% bovine serum albumin, and $10^{-4}$ 2-mercaptoethanol, to which was added 10% 5637 cell-conditioned medium and 2 U/mL or erythropoietin. Cultures were maintained at 37° C. in 5% $CO_2$ for 12 to 14 days. After scoring, colonies were processed individually or in pools for extractions of DNA. For certain experiments, IL-3 (10 ng/mL), IL-6 (50 ng/mL), and stem-cell factor (SCF) at 100 ng/mL (provided by Amgen, Thousand Oaks, Calif.) were used in place of 5637 cell-conditioned medium. Culture of rhesus bone marrow cells before and after CD34$^+$ immunoselection in methylcellulose was as described by Donahue, et al. (1992, J. Exp. Med. 175: 1125).

DNA isolation and analysis by the PCR-methodology—For preparation of DNA from hematopoietic colonies, single colonies were plucked and placed into 50 μL of diethylpyrocarbonate-treated water. Mineral oil was layered over the aqueous phase, and the samples were heated at 100° C. for 10 minutes and cooled to 4° C. Proteinase K (Pro-K) was added to a final concentration of 400 μg/mL and the samples were incubated at 55° C. for 90 minutes and then at 100° C. for five minutes (to inactivate Pro-K) before cooling to 4° C., DNA, for use as controls, was isolated by standard techniques from cultured cells or bone marrow mononuclear cells.

Standard PCR methodology for DNA analysis was performed using a kit provided by Perkin-Elmer/Cetus (Norwalk, Conn.) under the conditions specified by the manufacturer. Each 100 μL reactive contained 10 μL of the DNA preparation from individual or pooled colonies. [$^{32}$P] dCTP (800 Ci/mmol) (Amersham-Searle, Arlington Heights, Ill.) was added in the amount of 0.2 to 0.5 μL per reaction. Four hundred nanograms of each primer and 2.5 U of Taq DNA polymerase were also added to each 100 μL reaction. The PCR cycles for DNA analysis were preceded by incubation at 95° C. for 2 minutes, and then final cycle was followed by elongation at 72° C. for 7 minutes. Twenty-forty percent of each reaction mixture was analyzed on an 8% polyacrylamide gel that was processed for autoradiography.

A set of primers based on the sequence of the mouse β-actin coding region were used to amplify the human β-actin sequences to yield a 232 bp fragment. The sequences were as follows 5' primer, 5'-CATTGTGATGGACTCCGGAGACGG-3' (SEQ ID NO:3); and 3' primer, 5-CATCTCCTGCTCGAAGTCTAGAGC-3' (SEQ ID NO:4). The PCR was conducted for 25 cycles under the following conditions: 95° C. for 1 minute, 58° C. for 1 minute and 72° C. for 1.5 minutes. The sequences of the primer pair used to amplify a 314 bp segment of the, rhesus γ-globin gene are as follows: 5' primer, 5'-GTTGGGAGTGAAGAAACTGC-3' (SEQ ID NO:5); and 3' primer, 5'-TAGCCTCAGACTCTGTFGG-3' (SEQ ID NO:6). The PCR was conducted for 30 cycles under the following conditions: 94° C. for 1 minute, 55° C. for 1 minute and 72° C. for 1 minute. Another primer pair was used to amplify a 247-bp segment of the β-Gal gene. The sequences are as follows: 5' primer, 5'CTACACCAACGTAACCTATCCC-3' (SEQ ID NO:7) and 3' primer, 5' TTCTCCGGCGCGTAAAAATGCG-3' (SEQ ID NO:8). The PCR was conducted for 30 cycles under the following conditions, 94° C. for 1 minute, 55° C. for 1 minute and 72° C. for 1 minute.

Integration site analysis—The wild-type AAV genome was detected using the primer pair, 5' GAACGCGCAGC-CGCC (SEQ ID NO:9) and 5' GCGCATCAGAATTGG-GATC (SEQ ID NO:10) that gives a 635-bp amplification product derived from the 5' end of the AAV genome. PCR amplification was performed for 25 to 30 cycles under the conditions described below. AAV integration into chromosome 19 was detected by PCR using nested primer pairs that flank an AAV-chromosome 19 junction. Jus2 (AAV) -5'AGTAGCATGGCGGGT (SEQ ID NO:11) and Jus3 (chromosome 19) -5' CGCGCATAAGCCAGTAGAGCC (SEQ ID NO:12). PCR was for 25 cycles using previously described reaction conditions with the following parameters: 1 minute at 94° C., 1 minute at 55° C. and 2 minutes at 73° C. Two percent of the amplification product was diluted into a new reaction mixture containing a set of nested primers with G the following sequences: TR-1 (AAV), 5' GGAAT-TCAGGAACCCCTAGTGATGG (SEQ ID NO:13); and CR-2 (chromosome 19), -5' ACAATGGCCAGGGCCAG-GCAG (SEQ ID NO:14). The PCR parameters were the same as for the first amplification and 25 cycles were completed. The products were resolved on a 1% agarose gel, transferred to Hybond N+paper (Amersham), and probed with a previously cloned junction fragment labeled by Amersham Megaprime DNA labeling system. For molecular cloning of amplified junction fragments, the two nested primers from the second amplification, RT-1 and CR-2, were modified by incorporation of an EcoRI or BamHI restriction site, respectively. After amplification, the products were restricted with theses enzymes, purified on a 1% agarose gel, and subcloned into plasmids, pUC18 and pUC19, by standard methods. Sequencing was performed by the chain-termination method using a kit obtained from Promega.

2. Results

An AAV vector carrying the β-gal reporter gene was constructed to assay rAAV's transduction efficiency in various cell types. Addition of vector preparations at an MOI of 1 or greater to subconfluent Detroit 6 cells resulted in expression of the β-gal gene in most cells within 18 hours. The viral titers were estimated by adding serial dilutions to a fixed number of cells in each plate; individual preparations ranged from $10^4$ to $10^6$ infectious particles/mL. Similar results were obtained with vector lysates derived by $CaPO_4$-mediated gene transfer or by lipofection of the vector and helper (pAAV/Ad) plasmids: the titers of the two types of preparations did not vary in a consistent way. When the Detroit 6 cells were split twice and allowed to become confluent again, a much smaller portion of cells expressed the β-gal gene. Expressing cells were clustered, suggesting viral integration shortly after infection in a single cell that gave rise to a clone of expressing progeny.

Transduction of human erythroleukemia cells was also achieved with the rAAV-β-gal vector. Approximately 2% to 3% of cells exposed briefly to the virus at an MOI of approximately 1 expressed the β-gal gene 5 days later. Similarly, exposure of CD34+ immunoselected human progenitor cells to the virus for 3 days at an MOI of 1 to 10 resulted in expression of the β-gal gene in 60% to 70% of the cells. Control K562 or CD34+ selected cells showed no nuclear staining; low-level, nonspecific cytoplasmic staining was avoided by maintaining the pH of the washing buffer at greater than 7.5. These data established that viral uptake and rAAV mediated gene expression could be achieved at high efficiency in hematopoietic cells.

Figure 4:
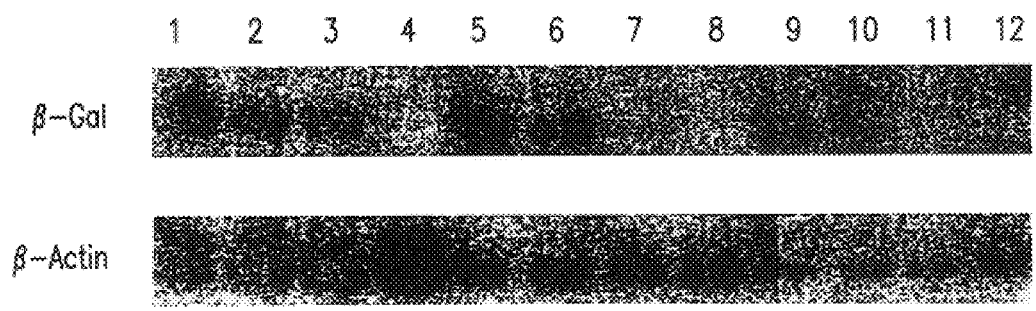
FIG. 4 shows calibration and sensitivity of the PCR reactions for detection of β-gal and β-actin coding sequences. Lanes 1 through 4 contain 1,000 ng of total DNA, lanes 5 through 8 contain 100 ng, and lanes 9 through 12 contain 10 ng. Each lane contains human DNA or mouse DNA form a cell line containing one integrated copy of the β-gal gene or mixtures thereof as follows: lane 1, 1,000 ng β-gal DNA; lane 2, 900 human DNA and 100 ng β-gal DNA; lane 3, 990 ng human DNA and 10 ng β-gal DNA: lane 4, 1,000 ng human DNA; lane 5, 100 β-gal DNA; lane 6, 90 ng human DNA and 10 ng β-gal DNA; lane 7, 99 ng human DNA and 1 ng β-gal DNA; lane 8, 100 ng human DNA; lane 9, 10 ng mouse β-gal DNA; lane 10, 9 ng human DNA and 1 ng β-gal DNA; lane 11, 9.9 ng human DNA and 0.1 ng β-gal DNA; lane 12, 10 ng human DNA. The β-actin coding sequences in mouse and human DNA amplified equivalently. The actin PCR product was generated with 25 cycles and visualized with a 20-minute exposure, whereas the β-gal-amplified PCR products were generated with 30 cycles and visualized with a 30-minutes exposure.

Attempts to detect β-gal activity in intact mature colonies are confounded by the fact that nuclear and cytoplasmic activities are not distinguished in intact colonies and background staining was variably high. Therefore a quantitative PCR assay is disclosed to detect the rAAV genome in individual colonies. A cell line having one integrated copy of the β-gal gene per cell was used as a control. Conditions were found for which the signal intensity generated with the β-gal primers was proportional to the concentration of the rAAV genome over a broad range of total DNA input (FIG. 4). The β-actin amplification could be used to verify that DNA from individual colonies gave a readily detectably PCR product and, by comparing its intensity to that of the β-gal PCR product, the copy number of the rAAV genome can be estimated.

Figure 5:
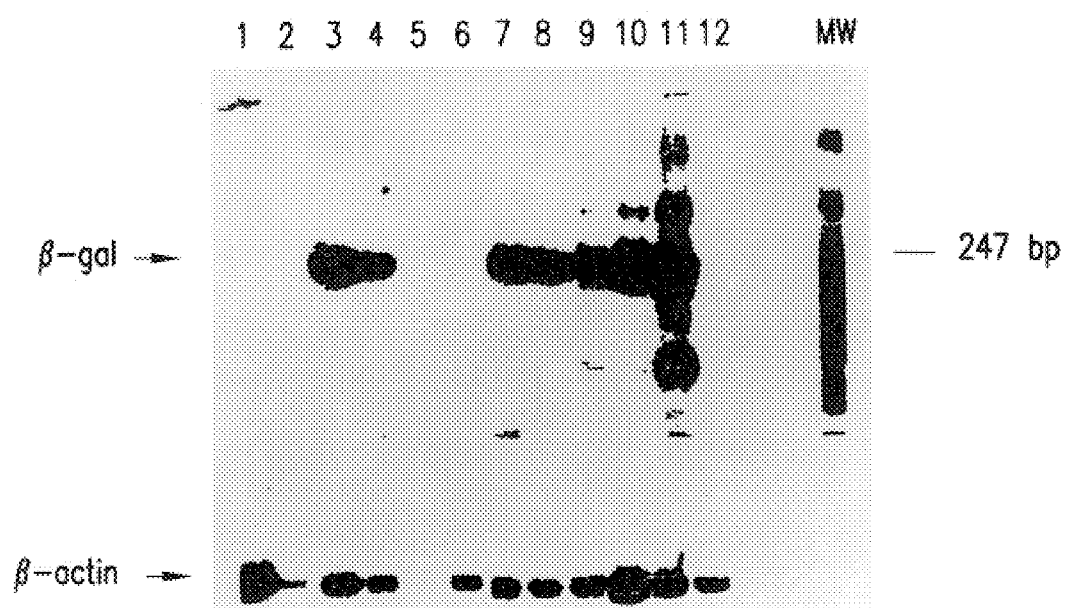
FIG. 5 shows the detection of the rAAV-β-Gal genome in individual human hematopoietic progenitor-derived colonies. DNA from 12 separate colonies were analyzed by PCR with primers specific for the β-gal or the β-actin coding sequences. One colony (5) was indeterminant, as the β-actin signal was not detectable. Seven of the remaining 11 colonies contained β-gal coding sequences and four were scored as negative.

FIG. 5 shows the application of this above-described technique to the analysis of colonies derived from human progenitors exposed to an rAAV virus preparation, after heating inactivation of adenovirus, at an MOI of approximately 1 for 24 hours. After the infection interval was completed, the cells were plated in methylcellulose under standard conditions. Individual colonies were plucked when mature at 12 to 14 days. DNA from seven colonies gave an amplified β-gal signal of a variable intensity, but in the range comparable to that of the β-actin control, suggesting that the viral genome was present at approximately single-copy equivalence in all cells of the colony. Four colonies were negative and one indeterminate (a β-actin signal was not generated from its DNA).

Figure 6:
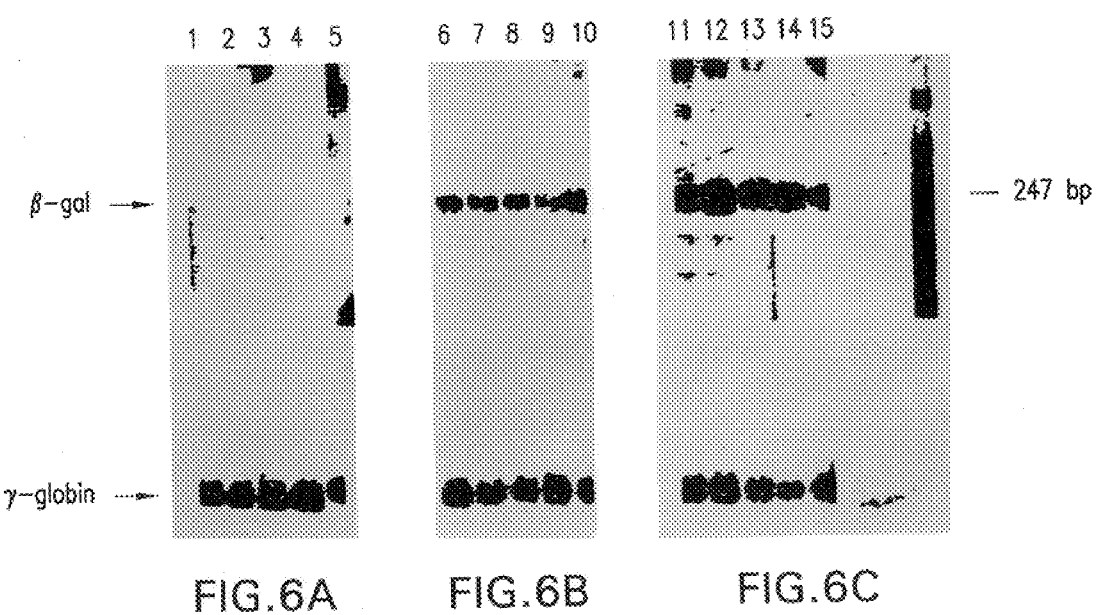
FIGS. 6A–6C show detection of the rAAV-β-Gal genome in hematopoietic colonies derived from rhesus progenitors. Shown are the results from 15 colonies in which the control primer pair for the rhesus γ-globin gene gave equivalent signals. (A) Five colonies lacking the β-gal coding sequences. (B) DNA from five colonies that gave a β-gal signal of intermediate intensity. (C) Five colonies in which the β-gal signals was equivalent or greater than that derived from the γ-globin gene.

FIGS. 6A–6C show an analogous experiment with CD34+ immunoselected rhesus hematopoietic progenitors infected with a vector preparation that had been heated for 1 hour at 55° C. to inactivate the adenovirus. At a low MOI, heat inactivation of the adenovirus appears to enhance the frequency of transfer of the rAAV genome. Results are shown for 15 colonies. Five were negative, five gave a signal intensity approximately 50% of that of gamma-globin, and the remaining five gave equivalent signal intensities with the two primer pairs. These data suggest that proviral copy number may vary among colonies, and raised the possibility that integration occurs in only a proportion of the initial cells derived from a single progenitor.

Figure 7:
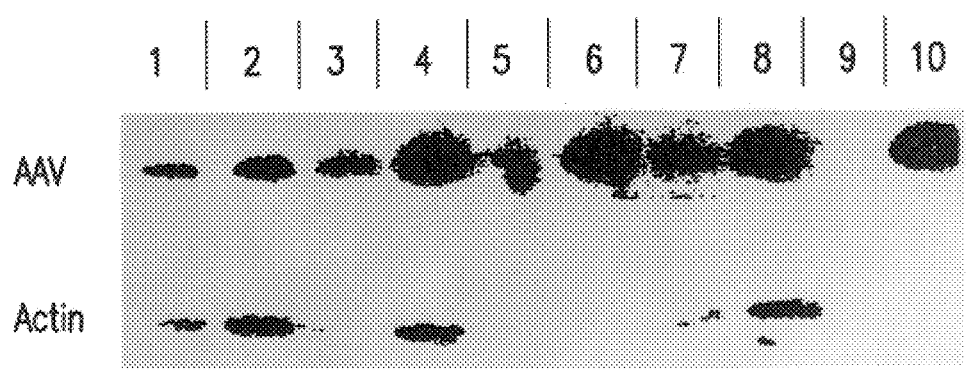
FIG. 7 shows integration of wild-type AAV into hematopoietic progenitors. DNA from 10 individual colonies was analyzed with primers specific for β-actin (control, below) and primers specific for the coding sequences of the AAV capsid protein. Eight colonies gave a positive signal, and two (5 and 9) were negative.

The present example shows that wild-type but not recombinant AAV integrates into a preferred region on chromosome 19. Human CD34+ immunoselected cells were exposed to wild-type virus preparations at high MOI (100 to 1,000). After culture for 36 hours in the presence of virus, progenitors were plated in methylcellulose and the colonies allowed to mature over 12 to 14 days. DNA from the majority of colonies (70% to 80%) generated an amplification product with a primer pair specific for AAV genome of intensity comparable to, or greater than, that achieved with the β-actin primers (FIG. 7). Because of the high estimated MOI, the potential that residual virus contributed to the signal for some colonies cannot be excluded. All colonies were derived from a single donor: the negative colonies establish that this individual was not harboring a latent AAV infection in bone marrow.

Figure 8A:
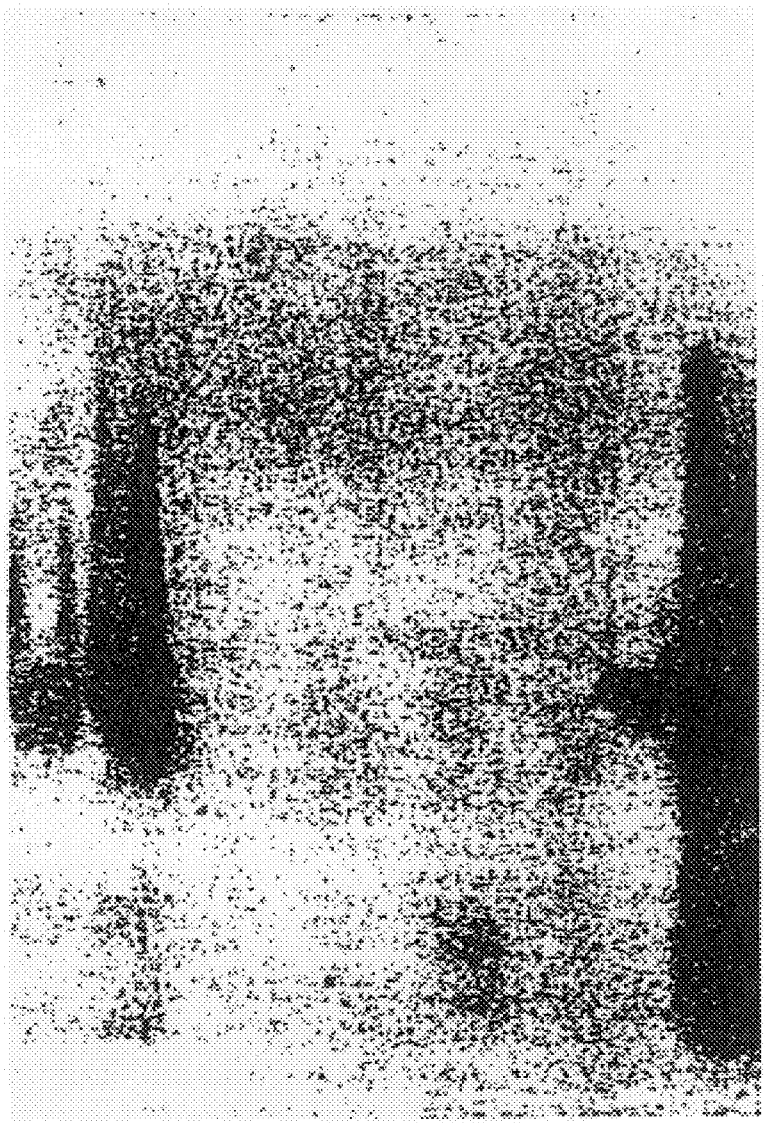
FIGS. 8A and 8B show integration site analysis of the wild-type AAV genome. DNA from pools of colonies or from single colonies was amplified using primer sets that span the potential junction between the AAV genome and the chromosome 190. Lanes 1, 2, 5, and 6 show DNA from pools of 40 to 80 individual colonies. Lanes 3 and 4 show DNA from single colonies. Lane 7 shows nonradioactive gel markers that gave the calibration lengths listed on the right. Lanes 8 and 9 show DNA from cell lines latently infected with the wild-type AAV genome. The multiple bands in lane 8 are thought to arise because the intact inverted terminal repeat present in this cell causes formation of several discrete PCR products. Amplification was performed with nested primers that span the putative integration junction as shown in the diagram.
Figure 8B:
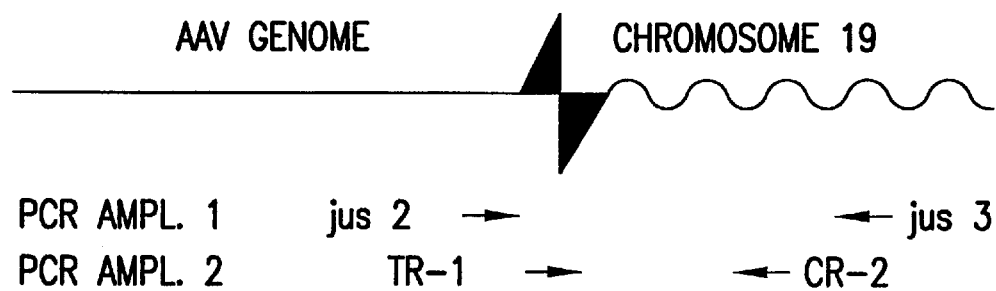

DNA from pools of 40 to 80 colonies or DNA from individual colonies were analyzed using two sets of nested primers that span the potential junction between to AAV genome and chromosome 19 DNA sequences. The pools and all of the colonies gave positive signals when analyzed for wild-type AAV DNA sequences by PCR. Duplicate samples from one pool gave a positive signal on the integration site analysis (FIGS. 8A and 8B). These PCR-amplified product were subcloned into a bacterial plasmid and the sequence determined. A novel junction was defined between the truncated inverted terminal repeat of AAV and chromosome 19DNA from 4 to 27 individual colonies, all of which were positive for wild-type AAV sequence, gave a junction amplification product that annealed to chromosome 19 and AAV genome probes. Three of these were also cloned and sequenced and shown to contain a novel junction between chromosome 19 and the AAV inverted terminal repair. These data show that association of wild-type viral DNA with progenitor-derived colonies with high frequency, but that site-specific integration of the AAV genome into chromosome 19 is relatively rare.

EXAMPLE III

This section exemplifies a main tenet of utilizing the rAAV vector constructs of the present invention to affect therapeutic relief or prophylactic intervention to various human diseases or disorders, both blood-borne and non blood-borne, which are amenable to tissue specific rAAV transduction and gene expression. To this end, it is shown in this Example the ability of an rAAV vector comprising the coding region for a Fanconi anemia C complementing (FACC) cDNA to direct phenotypic correction of Fanconi anemia.

Fanconi anemia (FA) is an autosomal recessive disorder characterized by pancytopenia, physical anomalies, and susceptibility to malignancy. Most patients are diagnosed in the first decade of life and die as young adults, usually from complications of severe bone marrow failure or, more rarely, from the development of acute leukemia or solid tumors. Therapy is currently limited to allogenic bone marrow transplantation from a histocompatible sibling, but most patients do not have an appropriate marrow donor.

The FACC cDNA has been shown to correct the phenotypic defect in tissue culture, resulting in normalized cell growth in the presence of MMC or DEB (Strathdee, et al., 1992, Nature (Lond.) 356:763–776). Because FA cells proliferate poorly, transfer of the FACC gene should provide a survival advantage to the gene-corrected FA cells, making this an ideal candidate for human gene therapy.

This Example discloses that the self-selecting growth advantage that the FACC gene confers allows for a functional assay to test gene transfer in FA(C) hematopoietic progenitor cells.

1. Material and Methods

Viruses and cells—Human adenovirus type 5 was is described in Example II. Epstein-Barr virus (EBV) transformed lymphoblast cell lines were obtained from Dr. Christopher Mathew (UMDS Guy's Hospital, London) and Dr. Manuel Buchwald (Hospital for Sick Children, Toronto). Detroit 6, 293, and K562 cells were maintained in Dulbecco's modified Eagle's medium (DMEM) containing 10% fetal calf serum (FCS), 2 mmol/L glutamine, 100 U/mL penicillin, and 0.1 mg/mL streptomycin.

Plasmids and DNA—The plasmid psub 201 is shown in FIG. 1B. The plasmid pAAV/Ad containing the entire coding sequence of AAV flanked with adenoviral terminal repeat sequences is described in Samulski, et al. (1989, J. Virol. 63: 3822–3828). The plasmid pUC008 contains a polylinker consisting of 5' NheI, XBaI, SalI, BglII, XhoI, ApaI, BamHI, XbaI, NheI 3'. The polylinker is subcloned into pUC9 between the XbaI and NheI restriction sites.

The plasmid pFAC3 was provided by Dr. Manual Buchwald. This plasmid contains the FACC cDNA within a pREP4 backbone. pREP4 (Invitrogen, San Diego, Calif.) contains an expression cassette containing the Rous sarcoma virus (RSV) 3' LTR and SV40 polyadenylation sequences.

Construction of rAAV plasmids—The FACC cDNA was excised from the plasmid pFAC3 after SalI digestion. This fragment was subcloned into pUC19-SalI. To remove the FACC 3' untranslated region, the pUC19 intermediate was digested with XbaI and NheI. These fragment ends were religated within the pREP4 polylinker, with the trimmed FACC lying between the RSV promoter and the SV40 polyadenylation site. The trimmed version of the FACC cDNA within the expression cassette derived from pREP4 was then subcloned into the SalI site of pUC008/Neo$^R$. The RSV-driven FACC cDNA and the TK-driven neomycin phosphotransferase gene were then excised from PUC008/Neo$^R$ with NheI and inserted into the XbaI site of psub201to create pAAV/FACC/Neo$^R$.

Generation of rAAV—Dishes (10 cm$^2$) containing 80% confluent 293 cells were infected with adenovirus type 5 at a multiplicity of 5–10 plaque forming units per cell. rAAV virons were generated by subsequent calcium phosphate cotransfection of 10 μg of pAAV/FACC/Neo$^R$ and 10 μg of helper plasmid (pAAV/Ad). Cells were harvested 40 hours posttransfection, frozen, and thawed four times, heat treated (56° C., 1 hour) to inactivate adenovirus, and centrifuge to remove celluiar debris.

Cell lysates were titered on D6 cells in the presence of 0.5 mg/mL Geneticin. Drug resistant colonies were isolated at 10–14 days. The rAAV titer was calculated from the number of resistant colonies and averaged 10$^4$–10$^5$ Neo$^R$ infectious particles per milliliter.

rAAV Infection of EBV-transformed Lymphoblasts—Lymphoblasts (1×10$^5$) were infected with cell lysate (3×10$^4$ Neo$^R$ infectious particles). Cells were harvested after 2d and grown in 15% fetal calf serum/RPMI with glutamine and antibiotics. Cells were passaged for 10d and then resuspended at 2×10$^9$ cells per ml in the presence of active G418 (0.2–0.6 mg/ml). Noninfected lymphoblasts yielded no viable cells following drug selection. Drug resistant cells were maintained in media containing G418for 3–4 weeks after infection.

Lymphoblast mitomycin C (MMC) sensitivity—Cellular sensitivity to mitomycin C was assayed by plating cells at a density of 2×10$^5$ per mL in 24-well plates. Increasing concentrations of MMC were added, and after a 5 day incubation, cellular viability was assayed via Trypan blue exclusion. Each sample was performed in quadruplicate.

Cynogenetic analysis of transduced lymphoblasts—Lymphoblast cultures were analyzed for cytogenetic breakage and radial formation by exposure to MMC (40 ng/ml final) for 2 d in the dark. Cultures were harvested after a 1 hour exposure to 0.25 μg/ml colcemid. After a 10 min treatment with 0.075 M KCL, the cells were fixed with a 3:1 mixture of methanol: acetic acid. Slides were prepared using wet slides, air dried and stained with Wright's stain. 50 metaphase figures from each culture were scored for obvious breaks, gaps larger than a chromatid width, and for radial formations.

Cell cycle analysis of transduced lymphoblasts—Lymphoblasts were plated at 2×10$^3$/ml and grown overnight. Either phosphate-buffered saline (PBS) or MMC (100 nM final concentration) was added and cells incubated for 24 hours A total of 1×10$^6$ cells were resuspended in 1.0 mL PBS with 2.0 ml cold 70% ethanol and incubated on ice for 30 min. Cells were centrifuged and cell pellet incubated with propidium iodide (20 μg/ml)/RNase A (0.04 mg.ml) solution for 20 min at room temperature before analysis on an Epics Elite (Coulter Electronics Inc., Hialeah, Fla.) flow cytometer. Data was analyzed using the multicycle software program based on the polynomial 5-phase algorithm (Phoenix Flow Systems, San Diego, Calif.).

Southern blot analysis of genomic DNA—Genomic DNA digestion and Southern transfer was performed using ammonium acetate buffer and Hybond N+ (Amersham Corp., Arlington Heights, Ill.) nylon filters. Blots were probed with a PstI (197 bp) P$^{32}$-labeled fragment of the neomycin phosphotransferase gene, Neo$^R$ (Stratagene, La Jolla, Calif.). Filters were washed to a final stringency of 2×SSC at 65° C. for 1 h.

Analysis of lymphoblast FACC expression—RNA was extracted from transduced lymphoblasts and 1.0 μg of RNA was reverse transcribed using the RNA PCR reagent kit (Perkin-Elmer Corp., Norwalk, Conn.). The cDNA sample was amplified using standard conditions including P$^{32}$dCTP. Primers specific for the endogenous FACC gene were: 5' CACAGACTATGGTCCAGGTGAAGG 3' (SEQ ID NO:15) and 5' ACCAGGAGTACCGAAGCTCACTTG 3' (SEQ ID NO:16). Primers specific for the transduced FACC gene were: 5;AATTACTGATGTCGGCAGCCGAAC and 3' (SEQ ID NO:17) and 5' TTATGATGTCTGGATCCGGC-CTTG 3' (SEQ ID NO:18). The amplification conditions used were: 95° C. for 30 s, 55° C. for 30 s, 72° C. for 1 min. and then a 72° C. extension for 8 min. PCR products were separated on a 5% polyacrylamide gel, dried, and autoradiographed.

Metabolic labeling and immunoprecipitation—[$^{35}$S] Methionine (100 μCi, 1,000 Ci/mnol) (Amersham Corp.) labeling of lymphoblasts (1×10$^2$ cells) was performed over 3 h and cells extracted in phosphate buffered saline, pH 7.5, containing 1% (vol/vol) Triton-X-100, aprotim (1 μg/ml ICN Biomedicals, Inc., Aurora, Ohio), leupeptin (1 μg/ml, ICN Biomedicals, Inc.), and AEBSF (10 μg/ml, ICN Biomedicals, Inc.). The extract was mixed with rabbit antiserum (1:200 dilution) raised against a glutathione S-transferase (GST)-FACC fusion protein (kindly provided by Dr. A. D'Andrea, Dana Farber Cancer Center). Immune complexes bound to protein A sepharose Cl-4B (Pharmacia, Piscataway, N.J.) were washed twice with 1% Triton X-100 and 0.1% SDS, and electrophoresed on a 10% SDS/polyacrylamide gel.

Isolation of CD34$^+$ hematopoietic cells—Apheresis was performed after obtaining written informed consent from patients enrolled on a protocol approved by the National Heart, Lung and Blood Institute Institutional Review Board. Peripheral blood (PB) cells were collected on a Fenwall CS3000 Blood Cell Separator. Mononuclear cells were obtained following Ficoll density gradient centrifugation and immunoselected on a Ceprate LC cell separation system (Cell Pro. Inc., Bothell, Wash.). Cells were incubated with a mouse IgM anti-human CD34, washed, and then incubated with a biotinylated goat anti-mous IgM antibody. Cells were filtered through an avidin column and observed cells eluted.

Cell purity was assessed by flow cytometric analysis A total of 2–4×10$^4$ cells were incubated at 4° C. for 30 min in 1% BSA with 10 μl phycoerythrin-conjugated anti-CD34 antibody (mouse anti-human HPCA2; Becton Dickinson, Mountview, Calif.). After they were washed, cells were analyzed on a Coulter Epics FACS. The percentage of cells staining for the CD34 antigen was compared with that of cells stained with isotypic control (IgG 2a mouse anti-human antibody; Becton Dickinson).

rAAV CD34$^+$ cell transduction and CFU-C assay- CD34$^+$ immunoselected cells were cultured at a density of 6×10$^4$ or 6×10$^3$ per ml in IMDM, 15% fetal calf serum containing 20 n./ml human interleukin-3 (IL-3, donated by Dr. Robert E. Donahue, Hematology Branch, NHLBI), 100 ng/ml human stem cell factor (SCF: Amgen Inc., Thousand Oaks, Calif.), and 50 ng/ml human interleukin 6 (IL-6 donated by Dr. Robert E. Donahue). rAAV lysate was added to maintain a multiplicity of infection of 0.1. Cells were incubated overnight, spun down and resuspended in fresh media and viral lysate. This protocol was repeated for 3 days Mock-infected cells grown only in media and colony stimulating factors served as controls.

After infection, 1×10$^5$ cells were plated in 3.0 ml methylcellulose (Terry Fox Labs, Vancouver, Canada) supplemented with SCF (100 ng/ml), IL-3 (20 ng/ml), IL-6 (50 ng/ml), and recombinant human erythropoietin (3 U/ml). Of this 3.0 ml mixture, 1.0 ml was plated in colony culture petri dishes (Nunc.). MMC was added directly to methylcellulose cultures to final concentrations of 1–10 nM. Cultures were grown in a humidified atmosphere at 37° C., and 5% CO. Colonies were counted at day 13.

Reverse transcriptase-polymerase chain reaction analysis of CFU-C Individual progenitor colonies containing 50–300 cells were harvested from methylcellulose into 30 μl of RNA Stat-60 (Tel-Test B Inc., Freindswood, Tex.) containing 10 μg transfer RNA and immediately frozen at −70° C. The RNA was isolated after chloroform extraction and precipitated with isopropanol. The sample was washed with ethanol, air dried, and resuspended in RNase-free water. An aliquot of each sample was reverse transcribed using the RNA PCR reagent kit (Perkin-Elmer Corp.) for 30 min at 42° C. Identical reactions without reverse transcriptase were performed. 20 μl of the cDNA generated was amplified using the manufacturer's recommended conditions and included P$^{32}$dCTP 800 Ci/mmol. Amersham Corp.). Primers mentioned previously were used for amplification. The conditions for amplification included: 95° C. for 2 min. and 72° C. for 2 min followed by extension at 72° C. for 8 min. PCR generated products were run on 5% polyacrylamide gels and autoradiographed.

Figure 10:
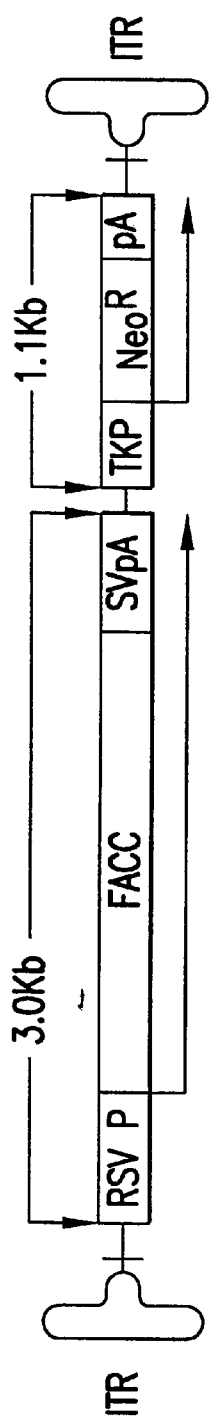
FIG. 10 shows construction of the rAAV/FACC/Neo$^R$ plasmid, with a Rous Sarcoma Virus (RVS) promoter. The FACC cDNA coding sequence was inserted into an expression cassette and linked to the Neo$^R$ gene. These transcription units were then subcloned into psub201. The orientation and size (kb) of each gene are indicated.
Figure 11:
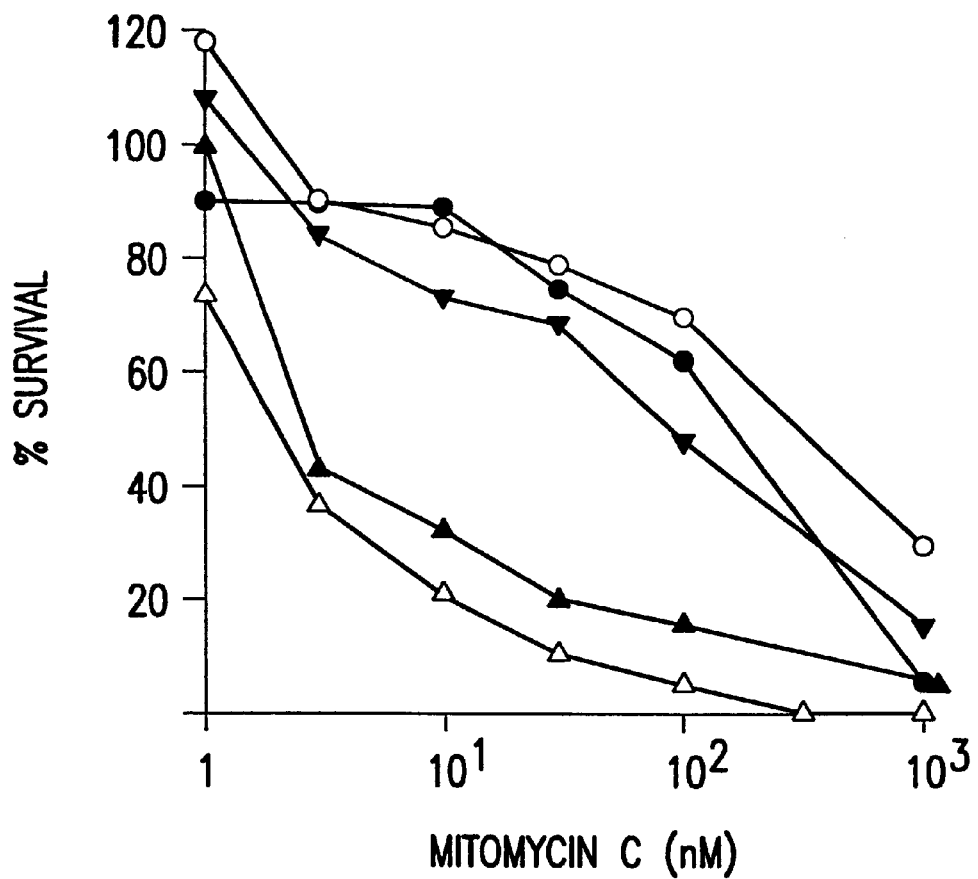
FIG. 11 shows analysis of rAAV/FACC-transduced lymphoblast mitomycin C sensitivity. Plot of cell viability of FA(C) lines, BD0215 (▼), HSC536 (Δ), normal lymphoblasts (○), rAAV/FACC-transduced BD0215 (▲), and rAAV FACC-transduced HSC536 (●) after incubation for 5 days with varying concentrations of MMC.

EBV-transformed lymphoblast cell lines derived from FA(C) patients was used to study in vitro gene complementation and functional correction of the FA defect. Two established cell lines from patients known to bear FACC mutant alleles were used to determine if a rAAV vector containing a copy of the normal FACC cDNA could correct the FA defect. The BD0215 lymphoblast cell line is homozygous for a nonsense mutation in exon 6 of the FACC coding sequence, which causes a premature termination of translation at amino acid residue 185, producing a truncated nonfunctional FACC protein. Lymphoblast cell line HSC536 contains a T to C transition leading to an amino acid substitution of leucine to proline (designated L554P). This mutation completely abolishes the activity of the FACC protein in functional assays (Gavish, et al. 1993, Hum. Moc. Gen. 2:123–126). Recombinant AAV virus, carrying the FACC cDNA in an expression cassette linked to the selectable gene Neo$^R$ (FIG. 10), was generated and used to infect FA(C) lymphoblast cell lines. G418-selected cells were used in functional complementation assays.

rAAV-mediated transfer and expression of the normal FACC gene corrected the defect in lymphoblast survival revealed by exposure to clastogenic agents such as MMC. Cells were incubated in the presence of varying concentrations of MMC for 5 d, and viable cells were counted. Parental cells were highly sensitive to DNA cross-linking agents with an EC$_{50}$ of 1.0–5.0 nM MMC. As shown in FIG. 11, cells transduced with rAAV were phenotypically altered so that the resistance of these lymphoblasts to MMC was comparable with that of normal lymphoblasts. The EC$_{50}$ of transduced cells was 100–500 nM, 100-fold higher than parental controls and comparable to the EC$_{50}$ of normal cells.

Hypersensitivity of FA cells to DNA cross-linking agents is known to result in an increased frequency of chromosomal breakage. rAAV-transduced cells were analyzed for chromosomal breakage after incubation in MMC. rAAV/HSC536 and rAAV/BD0215 cells had a significantly reduced number of chromosomal reaches and radials (<5%) compared with mock-infected parental cells ~50% of which had multiple chromosomal breaks and radial formation. The transduced cell lines no longer met the diagnostic criteria for FA, defined cytogenetically as >20% radial formation. Notably, these rAAV-transduced cells were routinely passaged without selection more than 50 times before use in the cytogenetic assay. This implied that stable integration of the rAAV provirus had occurred.

Figure 12B:
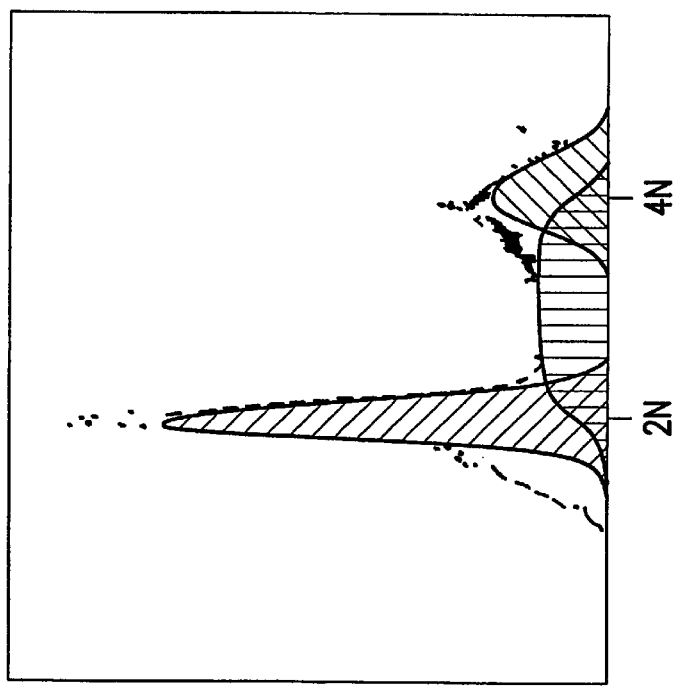
FIGS. 12A–12F show the effect of mitomycin C on DNA flow cytometry histograms of rAAV/Agamma globin/Neo-transduced lymphoblasts. The rAAV-transduced FA lymphoblast cell line (BD0215) was compared to the parental and normal lymphoblast cell lines. Cells were harvested, stained with propidium iodide, and DNA histograms were obtained 24 hours after cells were exposed to 100nM MMC (FIGS. 12B, 12D, and 12F).
Figure 12A:
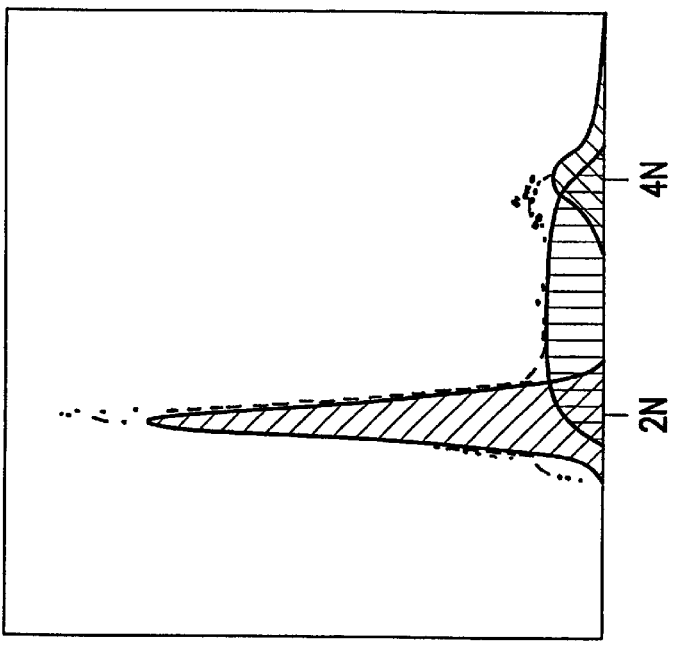
Figure 12D:
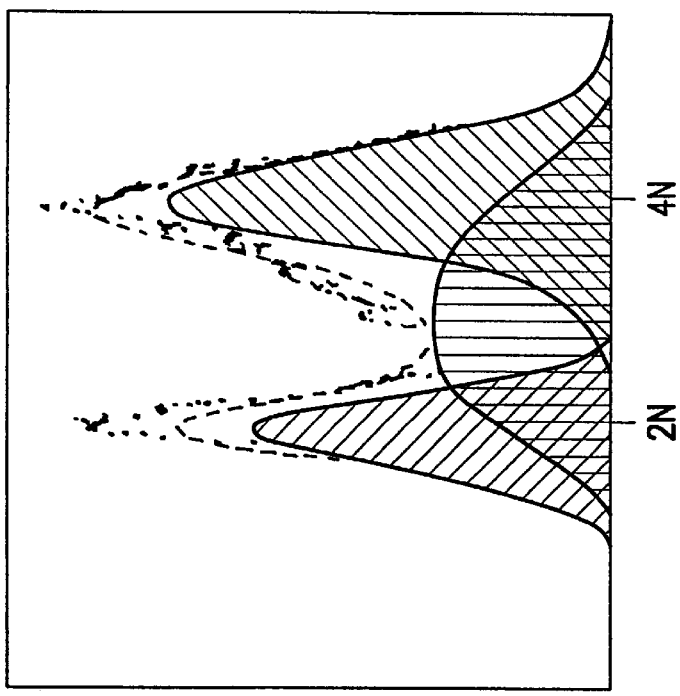
Figure 12C:
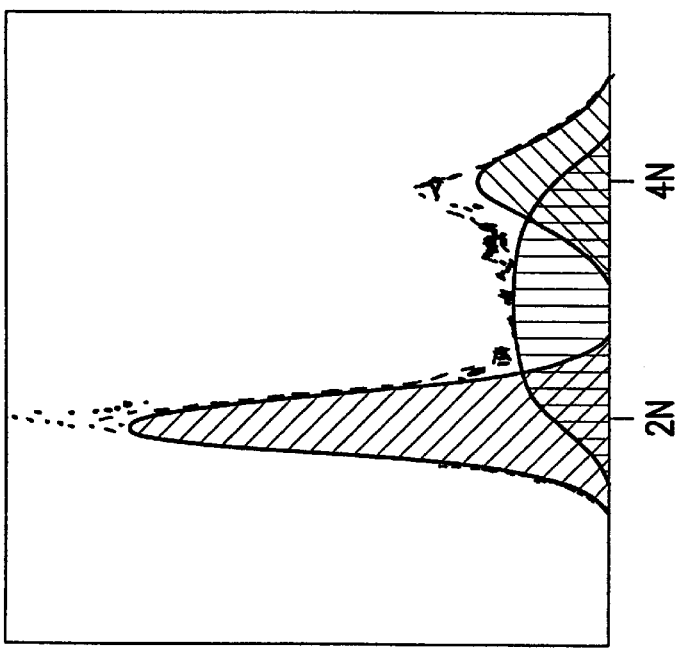
Figure 12E:
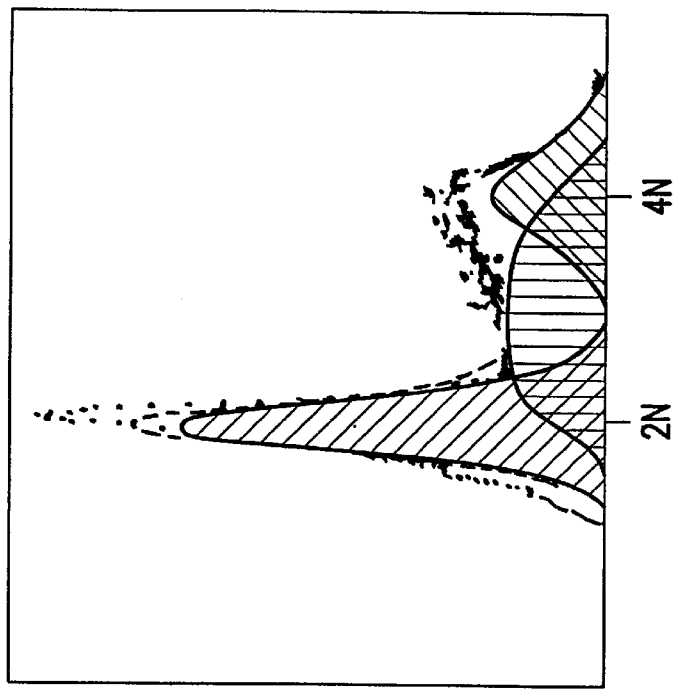
Figure 12F:
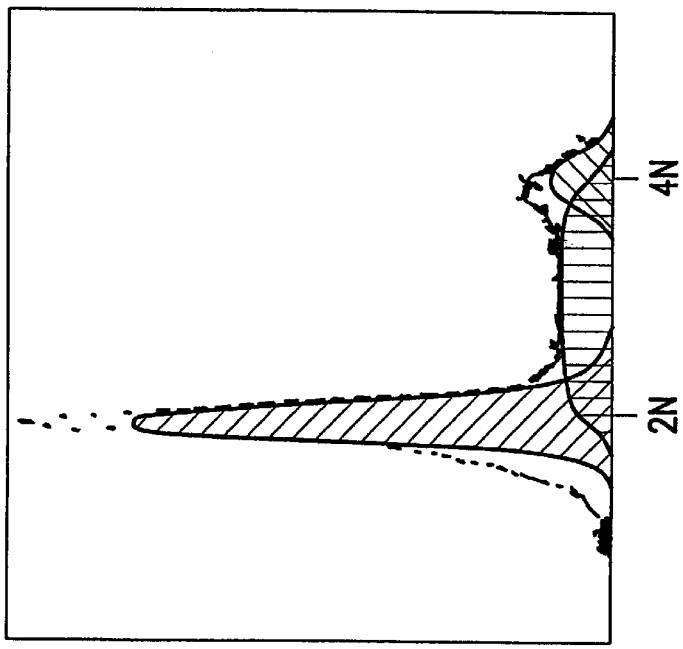
Figure 13A:
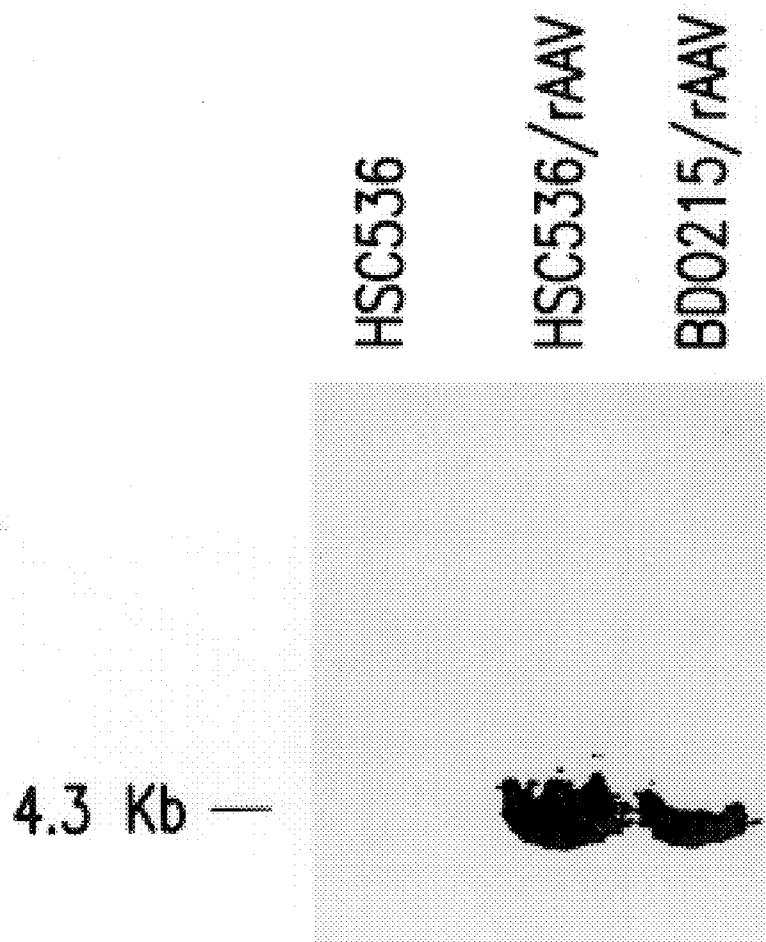
FIGS. 13A and 13B show southern blot analysis of FA(C) lymphoblasts infected with rAAV/FACC virus. (A) SnaBI digestion of genomic DNA isolated from rAAV/FACC-transduced BD0215, rAAV/FACC-transduced HSC536, and HSC536 cell lines. The expected 4.3-kb band represents an intact, unrearranged rAAV proviral form. HSC536 mock-infected cells served as a control DNA. (B) Schematic diagram of the integrated rAAV proviral form. The SnaBI restriction site located within each of the ITRs is indicated. A 197-bp Neo$^R$ fragment was used as a probe.
Figure 13B:
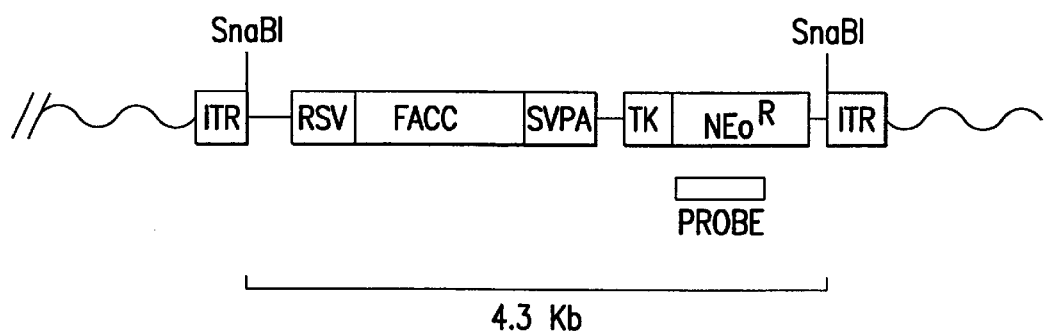

FA cells in each phase of the cell cycle were analyzed by propidum iodide staining and flow cytometry (FIGS. 12A–12F, Table II). The percentage of cells in the G2 phase is increased in FA patients as compared with normal individuals; this has been used diagnostically for evaluation of patients. The major effects of MMC on DNA flow histograms was the expected increase in the number of cells in G2 (see FIG. 4). Cell cycle analysis of lymphoblasts derived from a normal individual in the absence and presence of MMC (100 nM) indicated only a modest increase (8%) in the number of cells delayed in G2 phase (FIGS. 12A and 12B, and Table II). A marked delay in G2 transit was observed when the parental lymphoblast cell line BD0215 was incubated with MMC (FIGS. 12C and 12D). The percentage of cells in G2 increased from 16 to 41% (Table II). In marked contrast, cells from the rAAV-transduced FA line showed normalized cycle kinetics in both the absence or presence of MMC (FIGS. 12E and 12F, and Table II). No significant change in the number of cells in the S phase was observed at the concentration of MMC tested (shown in Table II).

rAAV-transduced cells selected in G418 were pooled and characterized by Southern blot analysis of genomic DNA. Southern analysis of DNAs from rAAV/FACC/Neo$^R$ transduced cells hybridized with a probe recognizing a fragment of neomycin phosphotransferase gene (FIGS. 13A and 13B). Digestion with SnaBI, which cuts within the termini, resulted in a single DNA band of predicated length, consistent with unrearranged integration of the provirus.

Figure 14A:
FIGS. 14A and 14B show expression of FACC mRNA in FA(C) lymphoblasts measured by the polymerase chain reaction. (A) Total RNAs isolated from rAAV-infected HSC536 and mock-infected HSC536 were analyzed for both endogenous and transduced FACC transcription. Primers specific for the endogenous FACC transcript (E) and the transduced FACC transcript (T) are indicated. RNA processed identically without reverse transcriptase (RT) and samples without RNA (labeled H$_2$O) served as negative controls. (B) The expected 602 or 486-bp products generated using reverse-transcribed RNA from the endogenous FACC gene and the transduced FACC gene, respectively.
Figure 14B:
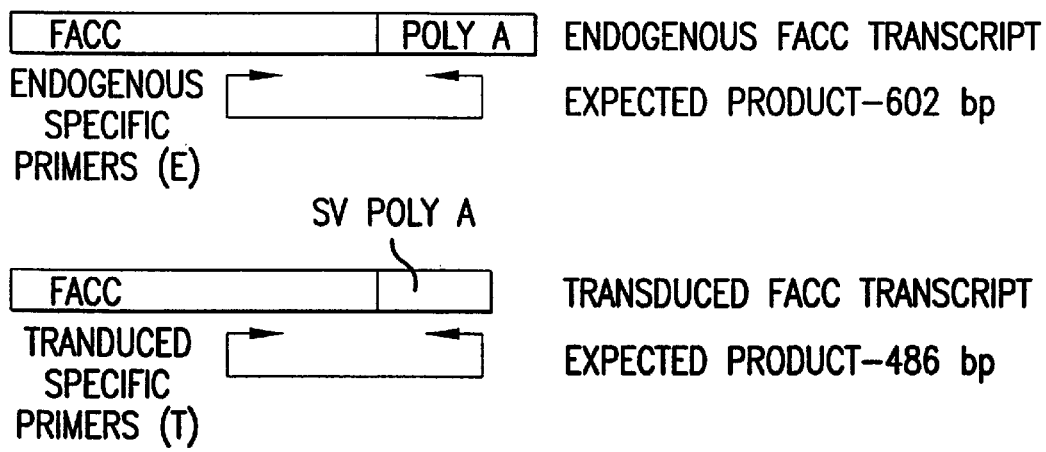

A reverse transcription (RT)-PCR assay was performed to determine the relative level of expression from both the transduced and endogenous FACC coding sequences. PCR primers, specified for the 3' untranslated sequences of the proviral and native FACC mRNAs, were designed to generate a 602-bp or a 486-bp product from the endogenous or transduced FACC gene, respectively. Total RNA isolated from lymphoblasts was reverse transcribed and the cDNA used for the PCR amplification (FIGS. 14A and 14B). An mRNA signal for the endogenous FACC product was obtained from mock-infected HSC536 celss. As expected, no mRNA signal was observed using primers for the transduced FACC gene. However, both the endogenous and proviral mRNAs were amplified by lymphoblasts transduced with rAAV/FACC/Neo$^R$.

Figure 15A:
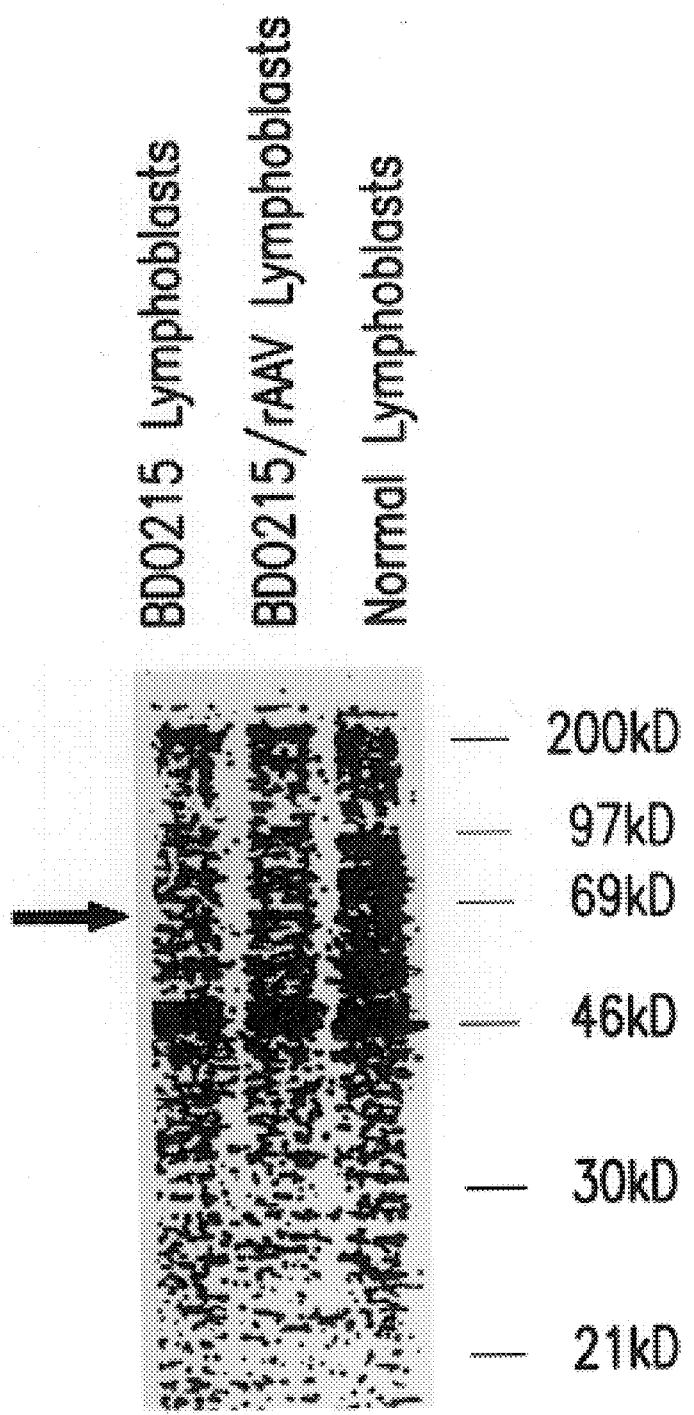
FIGS. 15A and 15B show immunoprecipitation analysis of normal, mutant (BD0215) and rAAV/transduced BD 0215 lymphoblasts. Cells were labeled with [$^{35}$S] methionine and radiolabeled proteins immunoprecipitated with anti-FACC antiserum. Proteins were resolved on a 10% SDS PAGE gel.
Figure 15B:
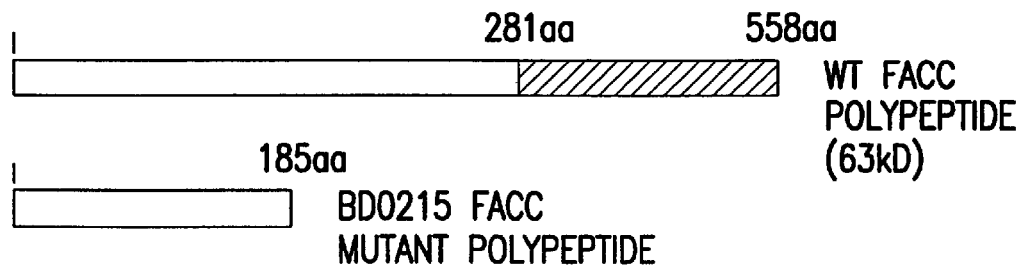

FACC protein expression in normal, parental BD0215, and transduced BD0215/rAAV lymphoblasts was analyzed by immunoprecipitation (FIGS. 15A and 15B). The rabbit polyclonal antierum used was generated from an epitope of a glutathione S-transferase (GST)-FACC fusion protein directed to the carboxy terminus of FACC (amino acids 281–558). The predicted 63-kD FACC protein was detected in both normal and transduced cell lines. As expected, no protein was detected from the parental line with a predicted truncated protein of 185 amino acids.

After the successful phenotypic correction of rAAV-transduced FACC lymphoblasts, we approached the problem of correcting the FACC defect in primary hematopoietic cells derived from a FA(C) patient. CD34$^+$ cells contain an enriched population of self-renewing stem cells, capable of sustaining long term bone marrow reconstitution. Peripheral blood mononuclear cells were obtained by apheresis from a FA(C) patient documented to have a splice mutation at FACC intron 4 (A to T) yielding a nonfunctional protein. Selected cells were isolated using a column containing an avidin-coated matrix that absorbs the human CD34-biotin-conjugated antibody. Flow cytometric analysis of the isolated cells revealed that 92% of the cells were CD34$^+$ after immunopurification. Cells were incubated with rAAV/FACC/Neo$^R$ at a multiplicity of infection (moi) of 0.1 for 3 d, washed, and 3×10$^4$ cells suspended in methylcellulose, as described in Methods. After a 15-d culture period, hematopoietic colonies derived from CD34-enriched cells were counted (See FIG. 16). Compared with mock-infected CD34$^+$ cells, cells incubated with virus yielded a fourfold increased number of colonies. Cells plated in media containing MMC (1.0 mM) yielded nearly an 8–10-fold increased number of measurable colonies, compared to nontransduced control cells incubated in MMC. Morphologically, the majority of colonies were of the myeloid/macrophage lineage (CFU-GM).

RT-PCR analysis was used to verify that the MMC progenitor colonies were transduced by rAAV. Apparent MMC resistant colonies were isolated; total RNA was obtained and analyzed by RT-PCR using conditions prescribed in this Example section. The autoradiograph in FIG. 17 demonstrates the appropriate 486-bp fragment in 6 of 9 colonies assayed. RNA not reverse transcribed generated no signal and ruled out the possibility of DNA contamination. Analysis of additional colonies demonstrated that 60% of colonies yielded the expected 486-bp signal without detectable contaminating DNA. Although the majority of colonies scored positive for rAAC/FACC expressions, some colonies did not express FACC as determined by our RT-PCR assay. RT-PCR results using β-actin primers generated the appropriate signal in all of the FA(C) colonies analyzed.

Therefore, Example III also exemplifies the essence of the present invention: A rAAV vector can adequately function as a gene transfer vehicle to treat a known human disorder. Particularly, the invention is herein exemplified by showing that a rAAV vector can transfer a functioning copy of the normal FACC gene to FA(C) lymphoblasts and CD34$^+$ hematopoietic progenitors, correcting the phenotypic defect of these cells. This phenotypic correction was determined by resistance of cells to MMC-induced cell death and in susceptibility to chromosomal breakage in lymphoblastoid cell lines.

It should be noted that >90% of the FA(C) immunoaffinity-purified cells were CD34 antigen positive, suggesting that primitive populations of hematopoietic cells can be transduced with rAAV. Unfortunately, the efficiency of rAAV transduction is difficult to accurately assess, particularly when the moi is quite low. We presume that colonies arose from transduced pluripotential cells but we have no way to ascertain what fraction of the CD34$^+$ population contain these cells. Therefore, it is reasonable to conclude that rAAV vectors are useful in gene transduction of hematopoietic progenitors and stem cells.

In vitro cultures assays of hematopoiesis in FAC patients have consistently shown a reduction or absence of colony forming progenitor cells (CFU-C) of all hematopoietic lineages (Sanders and Freeman 1978, Br. J. Haematol. 40:277–287; Alter, et al., 1992, Blood 80:3000–3008). Long-term bone marrow culture experiments, which require the development of an adherent stromal cell layer for the maintenance of progenitor growth, have also revealed a significant reduction in the number of CFU-C (Stark, et al., 1992, Br. J. Haematol, 83:554–559). Although defects of the bone marrow stromal elements cannot be totally excluded, fibroblasts (a major cell constituent of the stroma) from FA patients seem to express the appropriate repertoire of hematopoietic growth factors (Bagby, et al., 1993; Exp. Haemotol, 21–1419–1426). Available evidence suggests, therefore, that FA is a disorder of a primitive hematopoietic stem cell. We have been able to show that CD34$^+$ progenitors from a FA(C) patient retain the hypersensitivity to MMC which characterized cultured FA cells.

The unique characteristics of the FACC gene served as a biological marker in this Example for rAAV/FACC gene transfer. As we demonstrated with rAAV-transduced FA(C) lymphoblasts, expression of the FACC gene in FACC deficient cells promotes cell growth in the presence of MMC. The self-selected growth advantage conferred by expression of the FACC gene was also evident from the results obtained following the incubation of virally transduced FA(C) progenitor cells with low dose MMC (1 nM), a dose which has no effect on colony growth of CD34$^+$ cells from normal individuals. The increased colony growth reflects genetic rescue of CD34$^+$ progenitor cells after rAAV/FACC transduction. FACC gene expression detected from the majority of progenitor cell colonies provides presumptive evidence that the growth advantage was due to expression of the normal gene in cells bearing defective FACC alleles. Notably, even in the absence of MMC, rAAV transduced CD34$^+$ cells from normal individuals. The increased colony growth reflects genetic rescue of CD34$^+$ progenitor cells after rAAV/FACC transduction. FACC gene expression detected from the majority of progenitor cell colonies provides presumptive evidence that the growth advantage was due to expression of the normal gene cells bearing a defective FACC alleles. Notably, even in the absence of MMC, rAAV transduced CD34$^+$ cells yielded a fourfold greater number of viable progenitor colonies compared with mock-infected controls. Conversely, normal hematopoiesis is inhibited when the FACC gene is repressed using antisense oligonucleotides incubated with normal bone marrow cells (Segal, et al, 1993, Clin. Res. 41:276A). Therefore, the FACC gene may be involved in the maintenance of hematopoietic cell growth in addition to its role in the cellular response to DNA damage induced by agents such as MMC.

TABLE II

Cell Cycle Analysis of rAAV Transduced Lymphoblasts

| Cell Type | Condition | Cell Number | | |
|---|---|---|---|---|
| | | GI | S | G2 |
| Normal lymphoblast | −MMC | 58.8 | 32.5 | 8.7 |
| Normal lymphoblast | +MMC | 46.1 | 36.8 | 17.8 |
| BD0215 lymphoblast | −MMC | 51.4 | 32.2 | 16.4 |
| BD0215 lymphoblast | +MMC | 24.3 | 34.4 | 41.3 |
| BD0215/rAAV | −MMC | 59.6 | 31.4 | 9.1 |
| BD0215/rAAV | +MMC | 45.9 | 34.9 | 19.2 |

*Refers to the percentage of cells in the GI, S, and G-2 phases of cell cycle in the absence or presence of 100 nM MMC. Results are from duplicate samples from two experiments.

EXAMPLE IV

This section also exemplifies a main tenet of utilizing the rAAV vector constructs of the present invention to affect therapeutic relief or prophylactic intervention to various human blood-borne disorders. This portion of the present invention is exemplified by showing effective gene transfer and expression of another rAAV vector encoding the $^A\gamma^*$ globin gene under control of HS432.

1. Materials and Methods

Construction of Plasmid JM24/vHS432$^A\gamma^*$ and Preparation of rAAV—The human β-globin LCR fragments HS4, HS3, HS2, and the $^A\gamma^*$ globin gene were subcloned into pUC007. A BglII/SalI fragment of this construct was subcloned into pUC008, which was then digested with NheI and ligated to the XBaI fragment of psub201. FIG. 18A depicts the structure of the HS432$^A\gamma^*$ genome and the legend provides the details of fragments used in its construction. This plasmid construct, pJM24/vHS432$^A\gamma^*$, was contransfected with the complementing plasmid, pAAV!ad, into 293 cells previously infected with adenovirus type 5 to make the rAAV, vHS432$^A\gamma^*$. Preparation of cell lysates containing rAAV, Hirt extracts, and Southern blot analyses are described elsewhere (Samulski, et al., 1989, J. Virol. 63: 3822–3838; Hirt, 1967, J. Mol. Biol. 26: 365–369). All rAAV cell lysates were concentrated by ultrafiltration using a model 8400 stir cell apparatus and XM300 membrane (Amicon) prior to heat inactivation of adenovirus (56° C., 30 min). The final volume of concentrated cell lysate was ≈1 ml per 10-cm$^2$ dish of 293 cells used for contransinfection.

Assay for Estimation of rAAV particle Titer—Twenty microliters of rAAV cell lysate was incubated (37° C., 1 r) with 200 units of DNase (Boehringer Mannheim) in a final volume of 200 μl (20 mM Tris. HCl, pH 8.0/10 mM MgCl$_2$ buffer). DNase-protected particle (DPP) viral DNA was extracted with RNA STAT-60 (Tel-Test, Friendswood, Tex.) using the manufacturers's protocol with a final volume of 20 μl. This technique favors recovery of the low molecular weight single-stranded DNA genome of the rAAV vector particles. The polymerase chain reaction (PCR) generated a 665-bp fragment spanning the junction between HS2 and the $^A\gamma^*$ globin gene in HS432$^A\gamma^*$ (FIG. 18A). PCR conditions were as follows: 23 cycles; 95° C./1 min, 58° C./1 min 72° C./1.5 min; 5' primer, 5'-TCTCAGCCTAGAGTGATGAC; (SEQ ID NO:19)3' primer, 5'-ATAGTAGCCTTGTCCTCCTC (SEQ ID NO:20).

Preparation and Transduction of CD34$^+$ Selected Progenitor Cells—Human peripheral blood mononuclear cells were obtained by hemapheresis of a patient with Hb SS disease after informed consent under a protocol approved by Institute Review Board of the National Heart, Lung and Blood Institute. A Ceprate kit (CellPro, Bethell, Wash.) was used for CD34$^+$ cell enrichment according to the manufacture's protocol. One thousand CD34$^+$ selected cells were exposed to 500 μl of rAAV-containing cell lysate (10$^6$ particles) in a total volume of 1000 μl of tissue culture medium (Dulbecco a modified Eagle medium, 15% fetal calf serum, 50 ng of interleukin-6 per ml, and 100 ng of stem cell factor per ml). One transduction (see FIGS. 20A–20C) was done in tissue culture medium without growth factors. After an overnight exposure with gentle rocking at 37° C. in 5% CO$_2$, the cells were resuspended to 10$^3$ cells per ml and plated at 1000 cells per plate in methylcellulose containing growth factors (10 ng of granulocyte/macrophage colony-stimulating factor per ml, 10 ng of interleukin 3 per ml, 100 ng of stem cell factor per ml and 5 units of erythropoietin per ml). Cells were incubated at 37° C. in 5% CO$_2$ for 13–19 days prior to analysis of progenitor derived colonies.

Gene Transfer and Expression—RNA extraction from individual colonies was performed by placing each colony (<10 μl of methylcellulose) in 250 μl of Stat-60 (Tel-Test) according to the manufacturer's protocol and maintained at −70° C. until reverse transcriptase PCR (RT-PCR) analysis. RT-PCR reagents and the thermal-cycler were obtained from Perkin Elmer. The reverse transcriptase reactions (42° C./30 min, 95° C./5 min) were performed as single or double volume mixtures, followed by single or matched PCRs (35 cycles; 95° C./1 min, 60° C./1 min) using the appropriate primers. RNA-derived PCR mixtures, which included [$^{32}$P] CTP, were electrophoresed on 10% denaturing polyacrylamide gels and dried prior to autoradiogram or PhosphorImager analysis. Comparison of the polyacrylamide gel band intensities was made using the densitometry function of a PhosphorImager (Molecular Dynamics). High-performance liquid chromatography HPLC was used for Hb analysis as described by Fibach, et al., 1993, Blood 82: 162–165.

2. Results

Using the DPP titering assay, the concentration of rAAV genome in the cell lysate preparations was reproducibly estimated (FIG. 18B). DNase treatment was effective in eliminating amplification of plasmid and genomic DNA in the cell lysates. Control lysate samples were prepared from 293 cells cotransfected with the pJM24/vHS432$^A\gamma^*$ and pAAV/AD plasmids but not infected with adenovirus. The PCR amplified signals from these mock cell lysates were reduced to <1% of untreated samples by DNase treatment (FIG. 18B, lane 2). When the rAAV-containing lysates were extracted with Stat-60 (the commercial product contains phenol) prior to DNase treatment, the rAAV particle genomes were not protected by their capsids from DNase and therefore the signal was eliminated (FIG. 18B, lane 3). A standard curve was generated from the band intensities of PCR products amplified from serial dilutions of plasmid DNA, and the DPP titer of vHS432$^A\gamma^*$ lysates was estimated at 1–5×10$^6$ particles per ml. Stocks of vHS2/$^A\gamma$/neo$^R$ (FIG. 18B, lanes 7–9) were estimated to have a titer of 10$^6$ physical particles per ml by the DPP assay; these stocks had an infectious unit titer of ≈10$^4$ Neo$^R$ colonies on Detroit 6 cells in a standard biological titering assay. Thus, the DPP titering assay is consistent with previous data that predict a particle-to-infectious unit ratio of ≧100. Southern blot analysis of Hirt extracted DNA demonstrated the replicated forms of the vHS432$^A\gamma$* genome in 293 cells 24 hr after transduction (FIG. 18C).

These results have been reproduced in serval analyses of vHS432$^A\gamma$* transduced peripheral CD34$^+$ progenitor cells; a second experiment is shown in FIGS. 20A–20C. In the 19 erythroid colonies analyzed, equal amounts of cDNA were taken from a common RT reaction mixture and used as template for the PCR amplification of endogenous and $^A\gamma$* signals. As shown, evidence of transcription from the transduced rAAV genome was present in 7 or 19 colonies analyzed, and the $^A\gamma$* RNA-derived signals had intensities from 4% to 71% of those amplified using the same RT reaction mixture with primers specific for cDNA from the four endogenous γ-globin genes. The range of rAAV-derived and endogenous signal intensities in FIGS. 19A–19C and 20A–20C supports their use in providing a semiquantitative estimate of the level of rAAV transduced gene expression. The small amount of RNA available from each colony precluded other quantitative assays of transcriptional activity.

The results of HPLC analysis of the Hbs in colony erythroblasts are shown in FIGS. 21A–21C. The Hb composition of pooled colonies (>50 erythroid) derived from 1000 mock transduced progenitors was 26% HbF and 70% HbS, consistent with the high level of HbF production in erythroblasts derived from adult BFU-E when cultured in fetal serum containing medium. The HbF concentration in pooled colonies derived from an equal number of BFU-E transduced with vHS432$^A\gamma$* was 40% of the total. Since less than on-half of the colonies were expressing the vHS432$^A\gamma$* transferred gene, these data suggested a substantial increase in fetal Hb content in erythroblasts derived from transduced progenitors.

These data show the ability of rAAV to introduce a globin gene into primitive human hematopoietic cells and to express the gene in maturing erythroblasts without selection for cells in which the vector genome had been successfully introduced. The $^A\gamma$*-globin gene linked to the core elements of threes of the HSs from the β-globin gene cluster LCR was expressed at a level that approximated that of an endogenous globin gene. The conditions established for successful transduction of erythroid progenitors are potentially applicable to the ex vivo transduction of repopulating hematopoietic stem cells.

It will be appreciated by those persons skilled in the art that this invention provides a recombinant adeno-associated virus vector capable of delivering and expressing at least one mammalian gene into a genomne of a mammalian host cell wherein the expression of the gene is regulated in a tissue specific manner by the cis-acting regulatory and promoter elements. In addition, it will be understood by those persons skilled-in the art that this invention provides a method for using the recombinant adeno-associated virus vector of this invention for therapeutic purposes.

Further, it will be appreciated by those skilled in the art that additional hypersensitive sites and locus control regions may be effective in the recombinant adeno-associated virus vector of this invention.

Whereas particular embodiments of this invention have been described above for purposes of illustration, it will be evident to those persons skilled in the art that numerous variations of the details of the present invention may be made without departing from the invention as defined in the appended claims.

We claim:

1. A recombinant adeno-associated virus vector comprising:
   (a) at least a portion of the adeno-associated virus genome; and
   (b) a nucleic acid sequence encoding a mammalian Factor IX protein, wherein the expression of the mammalian Factor IX protein is regulated by a liver specific cis-acting regulatory element heterologous to the nucleic acid sequence encoding the mammalian Factor IX protein.

2. A recombinant adeno-associated virus vector of claim 1 in which the liver-specific cis-acting regulatory element is a eukaryotic cis-acting regulatory element.

3. The recombinant adeno-associated virus vector of claim 1, wherein the liver specific cis-acting regulatory element is a liver specific promoter.

4. The recombinant adeno-associated virus vector of claim 1, wherein the liver specific cis-acting regulatory element is a liver specific enhancer element.

5. The recombinant adeno-associated virus vector of claim 1 in which the mammalian Factor IX protein is human.

6. Transduced mammalian liver cells comprising a gene encoding mammalian Factor IX introduced in vitro into the genome of said mammalian cells by means of the recombinant adeno-associated virus vector of claim 1 or 2.

7. Transduced liver cells comprising a gene encoding mammalian Factor IX introduced in vitro into the genome of said liver cells by means of the recombinant adeno-associated virus vector of claim 1 or 2.

8. The transduced cells of claim 6 or 7 in which the mammalian Factor IX protein is human.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 1:

TCGCTTCTGG AACGTCTATC                    20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 2:

CACCTTCTTG CCATGTGCCT                    20

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 3:

CATTGTGATG GACTCCGGAG ACGG                             24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 4:

CATCTCCTGC TCGAAGTCTA GAGC                             24

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 5:

GTTGGGAGTG AAGAAACTGC                                  20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 6:

TAGCCTCAGA CTCTGTTTGC                                  20

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 7:

CTACACCAAC GTAACCTATC CC                               22

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 8:

TTCTCCGGCG CTTAAAAATG CG                                            22

(2) INFORMATION FOR SEQ ID NO: 9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 9:

GAACGCGCAG CCGCC                                                    15

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 10:

GCGCATCAGA ATTGGGATTC                                               20

(2) INFORMATION FOR SEQ ID NO: 11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 11:

AGTAGCATGG CGGGT                                                    15

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 12:

CGCGCATAAG CCAGTAGAGC C                                             21

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single (D) TOPOLOGY: linear (ii) MOLECULE TYPE: oligonucleotide (xi) SEQUENCE DESCRIPTION: SEQ ID NO: 13:

GGAATTCAGG AACCCCTAGT GATGG                                        25

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 14:

ACAATGGCCA GGGCCAGGCA G                                            21

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 15:

CACAGACTAT GGTCCAGGTG AAGG                                         24

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 16:

ACCAGGAGTA CCGAAGCTCA CTTG                                         24

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 17:

AATTACTGAT GTCGGCAGCC GAAC                                         24

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide -continued (xi) SEQUENCE DESCRIPTION: SEQ ID NO: 18:

TTATGATGTC TGGATCCGGC CTTG                                          24

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 19:

TCTCAGCCTA GAGTGATGAC                                               20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 20:

ATAGTAGCCT TGTCCTCCTC                                               20